United States Patent
Scheuing et al.

(10) Patent No.: US 9,309,435 B2
(45) Date of Patent: *Apr. 12, 2016

(54) PRECURSOR POLYELECTROLYTE COMPLEXES COMPOSITIONS COMPRISING OXIDANTS

(71) Applicant: The Clorox Company, Oakland, CA (US)

(72) Inventors: David R. Scheuing, Pleasanton, CA (US); Thomas F. Fahlen, Pleasanton, CA (US); Jared Heymann, Pleasanton, CA (US); Mike Kinsinger, Pleasanton, CA (US); William Ouellette, Pleasanton, CA (US); William L. Smith, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/772,674

(22) Filed: Feb. 21, 2013

(65) Prior Publication Data

US 2013/0165572 A1 Jun. 27, 2013

Related U.S. Application Data

(63) Continuation-in-part of application No. 12/749,288, filed on Mar. 29, 2010, now abandoned, which is a continuation-in-part of application No. 13/046,385, filed on Mar. 11, 2011.

(51) Int. Cl.
*C09D 133/00* (2006.01)
*C11D 1/65* (2006.01)
(Continued)

(52) U.S. Cl.
CPC ............... *C09D 147/00* (2013.01); *C09D 5/14* (2013.01); *C09D 133/02* (2013.01); *C11D 3/378* (2013.01);
(Continued)

(58) Field of Classification Search
CPC .................................. C11D 1/65; C11D 3/395
See application file for complete search history.

(56) References Cited

U.S. PATENT DOCUMENTS

| 3,896,056 A | * | 7/1975 | Benjamin et al. | 510/357 |
| 3,950,260 A | * | 4/1976 | Eldib | C11D 3/3757 510/237 |

(Continued)

FOREIGN PATENT DOCUMENTS

| EP | 0342997 B2 | 5/1989 |
| WO | 01/23511 A1 | 4/2001 |

(Continued)

OTHER PUBLICATIONS

Chua (Wal-Mart to Sell Only Concentrated Laundry Detergent Category by 2008, Jasmin Malik Chua, Oct. 1, 2007, http://www.treehugger.com/corporate-responsibility/wal-mart-to-sell-only-concentrated-laundry-detergent-category-by-2008.html, Retrieved Jun. 12, 2013).*

(Continued)

*Primary Examiner* — Francisco Tschen
(74) *Attorney, Agent, or Firm* — Alok Goel

(57) ABSTRACT

The invention relates to compositions and methods of treatment employing compositions comprising polyelectrolyte complexes. The compositions include a water-soluble first polyelectrolyte bearing a net cationic charge or capable of developing a net cationic charge and a water-soluble second polyelectrolyte bearing a net anionic charge or capable of developing a net anionic charge. The total polyelectrolyte concentration of the first solution is at least 110 millimolar. The composition is free of coacervates, precipitates, latex particles, synthetic block copolymers, silicone copolymers, cross-linked poly(acrylic) and cross-linked water-soluble polyelectrolyte. The composition may be a concentrate, to be diluted prior to use to treat a surface.

3 Claims, 1 Drawing Sheet

(51) Int. Cl.

| | | |
|---|---|---|
| *A61K 8/73* | (2006.01) | |
| *C09D 147/00* | (2006.01) | |
| *C09D 133/02* | (2006.01) | |
| *C09D 5/14* | (2006.01) | |
| *C11D 3/37* | (2006.01) | |
| *C11D 3/48* | (2006.01) | |

(52) U.S. Cl.
CPC ............ *C11D 3/3757* (2013.01); *C11D 3/3765* (2013.01); *C11D 3/3769* (2013.01); *C11D 3/3773* (2013.01); *C11D 3/3776* (2013.01); *C11D 3/48* (2013.01)

(56) References Cited

U.S. PATENT DOCUMENTS

| | | | |
|---|---|---|---|
| 4,147,649 A | 4/1979 | Arnau et al. | |
| 4,301,067 A | 11/1981 | Koshugi | |
| 4,501,834 A | 2/1985 | Su | |
| 4,501,835 A | 2/1985 | Berke | |
| 4,681,696 A | 7/1987 | Bruegge | |
| 4,710,374 A | 12/1987 | Grollier et al. | |
| 4,999,386 A | 3/1991 | Oakes et al. | |
| 5,049,383 A | 9/1991 | Huth et al. | |
| 5,158,766 A | 10/1992 | Greenwald et al. | |
| 5,578,598 A | 11/1996 | Abe et al. | |
| 5,700,559 A | 12/1997 | Sheu et al. | |
| 5,858,938 A | 1/1999 | Glen, Jr. et al. | |
| 5,874,524 A | 2/1999 | Pakusch et al. | |
| 6,017,561 A | 1/2000 | Zhou et al. | |
| 6,028,043 A | 2/2000 | Glen, Jr. et al. | |
| 6,221,399 B1 | 4/2001 | Rofles et al. | |
| 6,270,754 B1 | 8/2001 | Zhou et al. | |
| 6,638,918 B2 | 10/2003 | Davison et al. | |
| 6,703,358 B1 | 3/2004 | Aubay et al. | |
| 6,743,775 B2 | 6/2004 | Santar et al. | |
| 6,838,078 B2 | 1/2005 | Wang et al. | |
| 6,849,586 B2 | 2/2005 | Avery et al. | |
| 6,887,564 B2 | 5/2005 | Gagliardini et al. | |
| 6,939,554 B2 | 9/2005 | McDonald et al. | |
| 7,018,709 B2 | 3/2006 | Stevenson et al. | |
| 7,141,617 B2 | 11/2006 | Gratson et al. | |
| 7,288,514 B2 | 10/2007 | Scheuing et al. | |
| 7,511,008 B2 | 3/2009 | Scheuing et al. | |
| 8,728,454 B1 | 5/2014 | Scheuing | |
| 8,728,530 B1 | 5/2014 | Scheuing | |
| 8,765,114 B2 | 7/2014 | Scheuing | |
| 8,883,705 B2 | 11/2014 | Scheuing | |
| 8,883,706 B2 | 11/2014 | Scheuing | |
| 8,933,010 B2 | 1/2015 | Scheuing | |
| 8,975,220 B1 | 3/2015 | Kaur | |
| 8,993,505 B2 | 3/2015 | Scheuing | |
| 9,012,389 B2 | 4/2015 | Scheuing | |
| 9,045,719 B1 | 6/2015 | Kaur | |
| 2001/0003221 A1* | 6/2001 | Akbarian et al. | 8/137 |
| 2001/0056058 A1* | 12/2001 | Panandiker et al. | 510/475 |
| 2002/0010105 A1 | 1/2002 | Bacon et al. | |
| 2002/0010124 A1* | 1/2002 | Creeth | C11D 1/008 |
| | | | 510/475 |
| 2002/0019328 A1 | 2/2002 | Schroeder | |
| 2002/0049149 A1 | 4/2002 | Durbut et al. | |
| 2002/0082181 A1 | 6/2002 | Humphrey | |
| 2002/0151454 A1* | 10/2002 | Kischkel et al. | 510/466 |
| 2002/0169097 A1 | 11/2002 | Kasturi et al. | |
| 2003/0059398 A1 | 3/2003 | Ranger et al. | |
| 2003/0064905 A1* | 4/2003 | Gohl | C11D 1/83 |
| | | | 510/352 |
| 2003/0114342 A1 | 6/2003 | Hall | |
| 2003/0147826 A1 | 8/2003 | Anthony et al. | |
| 2003/0176306 A1 | 9/2003 | McKechnie | |
| 2003/0183253 A1 | 10/2003 | Cornelius | |
| 2003/0216281 A1 | 11/2003 | DeLeo et al. | |
| 2003/0228992 A1* | 12/2003 | Smets | C11D 3/001 |
| | | | 510/267 |
| 2004/0013638 A1 | 1/2004 | Aubay et al. | |
| 2004/0052748 A1 | 3/2004 | Vondruska | |
| 2004/0103483 A1 | 6/2004 | Delplancke et al. | |
| 2004/0138084 A1* | 7/2004 | Gohl | C11D 1/835 |
| | | | 510/417 |
| 2004/0149315 A1 | 8/2004 | Kim | |
| 2004/0152617 A1 | 8/2004 | Murphy et al. | |
| 2004/0170587 A1 | 9/2004 | Vondruska | |
| 2004/0194800 A1 | 10/2004 | Chang et al. | |
| 2004/0221873 A1 | 11/2004 | Rusciolelli | |
| 2005/0008534 A1 | 1/2005 | Hodge et al. | |
| 2005/0009971 A1 | 1/2005 | Hodge et al. | |
| 2005/0013794 A1 | 1/2005 | Hodge et al. | |
| 2005/0014670 A1 | 1/2005 | Hodge et al. | |
| 2005/0026801 A1 | 2/2005 | Broeckx et al. | |
| 2005/0096239 A1 | 5/2005 | Barnabas et al. | |
| 2005/0154361 A1 | 7/2005 | Sabesan | |
| 2005/0159321 A1 | 7/2005 | Cusack et al. | |
| 2005/0182021 A1 | 8/2005 | Nichols et al. | |
| 2005/0204477 A1* | 9/2005 | Casella et al. | 8/115.51 |
| 2005/0233938 A1* | 10/2005 | Delplancke et al. | 510/507 |
| 2006/0035805 A1* | 2/2006 | Penninger | 510/473 |
| 2006/0035807 A1* | 2/2006 | Kasturi et al. | 510/475 |
| 2006/0058214 A1 | 3/2006 | Zhang et al. | |
| 2006/0073994 A1 | 4/2006 | Hage | |
| 2006/0074005 A1 | 4/2006 | Kischkel et al. | |
| 2006/0275337 A1* | 12/2006 | Cohen Stuart et al. | 424/423 |
| 2006/0276371 A1 | 12/2006 | Schreiner et al. | |
| 2007/0054828 A1 | 3/2007 | Gentschev | |
| 2007/0259800 A1 | 11/2007 | Boutique et al. | |
| 2007/0293414 A1* | 12/2007 | Panandiker et al. | 510/515 |
| 2008/0108537 A1* | 5/2008 | Rees | 510/258 |
| 2008/0148491 A1 | 6/2008 | van Buskirk | |
| 2008/0206293 A1 | 8/2008 | Toreki | |
| 2010/0237282 A1 | 9/2010 | Komatsu et al. | |
| 2010/0316715 A1 | 12/2010 | Andersson | |
| 2011/0236450 A1 | 9/2011 | Scheuing | |
| 2011/0236582 A1 | 9/2011 | Scheuing | |
| 2013/0165525 A1 | 6/2013 | Scheuing | |
| 2013/0165572 A1 | 6/2013 | Scheuing | |
| 2013/0216293 A1 | 8/2013 | Garner | |
| 2013/0216631 A1 | 8/2013 | Garner | |
| 2013/0217610 A1 | 8/2013 | Garner et al. | |
| 2013/0273174 A1 | 10/2013 | Scheuing | |
| 2014/0116917 A1 | 5/2014 | Scheuing | |
| 2014/0116918 A1 | 5/2014 | Scheuing | |
| 2014/0120054 A1 | 5/2014 | Scheuing | |
| 2014/0120055 A1 | 5/2014 | Scheuing | |
| 2014/0120056 A1 | 5/2014 | Scheuing | |
| 2014/0121281 A1 | 5/2014 | Scheuing | |
| 2014/0200300 A1 | 7/2014 | Scheuing | |
| 2014/0212511 A1 | 7/2014 | Scheuing | |
| 2014/0296126 A1 | 10/2014 | Scheuing | |
| 2015/0038392 A1 | 2/2015 | Scheuing | |
| 2015/0264922 A1 | 9/2015 | Scheuing | |

FOREIGN PATENT DOCUMENTS

| | | |
|---|---|---|
| WO | 03/068843 A1 | 8/2003 |
| WO | 2004/041986 A1 | 5/2004 |
| WO | 2005/044967 A2 | 5/2005 |
| WO | 2005/072712 A2 | 8/2005 |
| WO | 2005/092273 A2 | 10/2005 |
| WO | WO 2007009917 A1 * | 1/2007 |
| WO | 2007/022235 A1 | 2/2007 |
| WO | 2008/134212 A1 | 11/2008 |

OTHER PUBLICATIONS

Dautzenberg (Dautzenberg, H., Polyelectrolyte Complex Formation in Highly Aggregating Systems. 1. Effect of Salt: Polyelectrolyte Complex Formation in the Presence of NaCl, Macromolecules 1997, 30, 7810-7815).*
Stuart et al. Colloids & Surfaces 242 (2004) 167-174.
Stuart et al. Langmuir 2004 (20) 1073-1084.
Tiller European Coatings Journal-BIOCIDES-12 (06) 28-32.
Buchhammer et al. Colloids & Surfaces 122 (1997) 1-12.
Buchhammer et al. Colloids & Surfaces 137 (1998) 45-56.
Buchhammer et al. Colloids & Surfaces 140 (1998) 377-384.

(56) References Cited

OTHER PUBLICATIONS

Buchhammer et al. Colloids & Surfaces 218 (2003) 151-159.
Buchhammer et al. Colloid Polym Sci 278 (2000) 841-847.
International Search Report of PCT Application No. PCT/US 2011/29530, May 27, 2011, 3 Pages.
International Search Report of PCT Application No. PCT/US 2011/29459, Jun. 3, 2011, 4 Pages.
Zintchenko et al., Polyelectrolyte Complex Formation with Double Hydrophilic Block Polyelectrolytes: Effects of the Amount and Length of the Neutral Block, Langmuir 2002, 18, 1386-1393.
Kitchen Clean-Up, EC 1552-E, Oregon State University Extension Service, Published Sep. 2002.
Stefan van der Burgh et al; "Complex coacervation core micelles as anti-fouling agents on silica and polystyrene surfaces"; Elsevier; Colloids and Surfaces A: Physiochem.Eng. Aspects 242 (2004); pp. 167-174; www.elsevier.com.
US Final Rejection, issued Nov. 17, 2014, from U.S. Appl. No. 14/227,272, filed Mar. 27, 2014.
US Final Rejection, issued Nov. 17, 2014, from U.S. Appl. No. 14/227,363, filed Mar. 27, 2014.
International Search Report, mailed Nov. 19, 2014 from PCT/US 14/50577, filing date Aug. 11, 2014.
US Non-Final Rejection, dated Jun. 26, 2013, from U.S. Appl. No. 13/046,385, filed Mar. 11, 2011.
US Final Rejection, dated Oct. 22, 2013, from U.S. Appl. No. 13/046,385, filed Mar. 11, 2011.
US Non-Final Rejection, dated Aug. 4, 2014, from U.S. Appl. No. 14/227,272, filed Mar. 27, 2014.
US Non-Final Rejection, dated Aug. 13, 2014, from U.S. Appl. No. 14/277,363, filed Mar. 27, 2014.
US Non-Final Rejection, dated Sep. 30, 2014, from U.S. Appl. No. 14/456,420, filed Aug. 11, 2014.
ACI (www.cleaninginstitute.org/clean_living/laundering-problems.aspx, retrieved Nov. 19, 2015, published online Feb. 1, 2001).
US Non-final Rejection, issued on Nov. 30, 2015, from U.S. Appl. No. 13/772,733, filed Feb. 21, 2013.

* cited by examiner

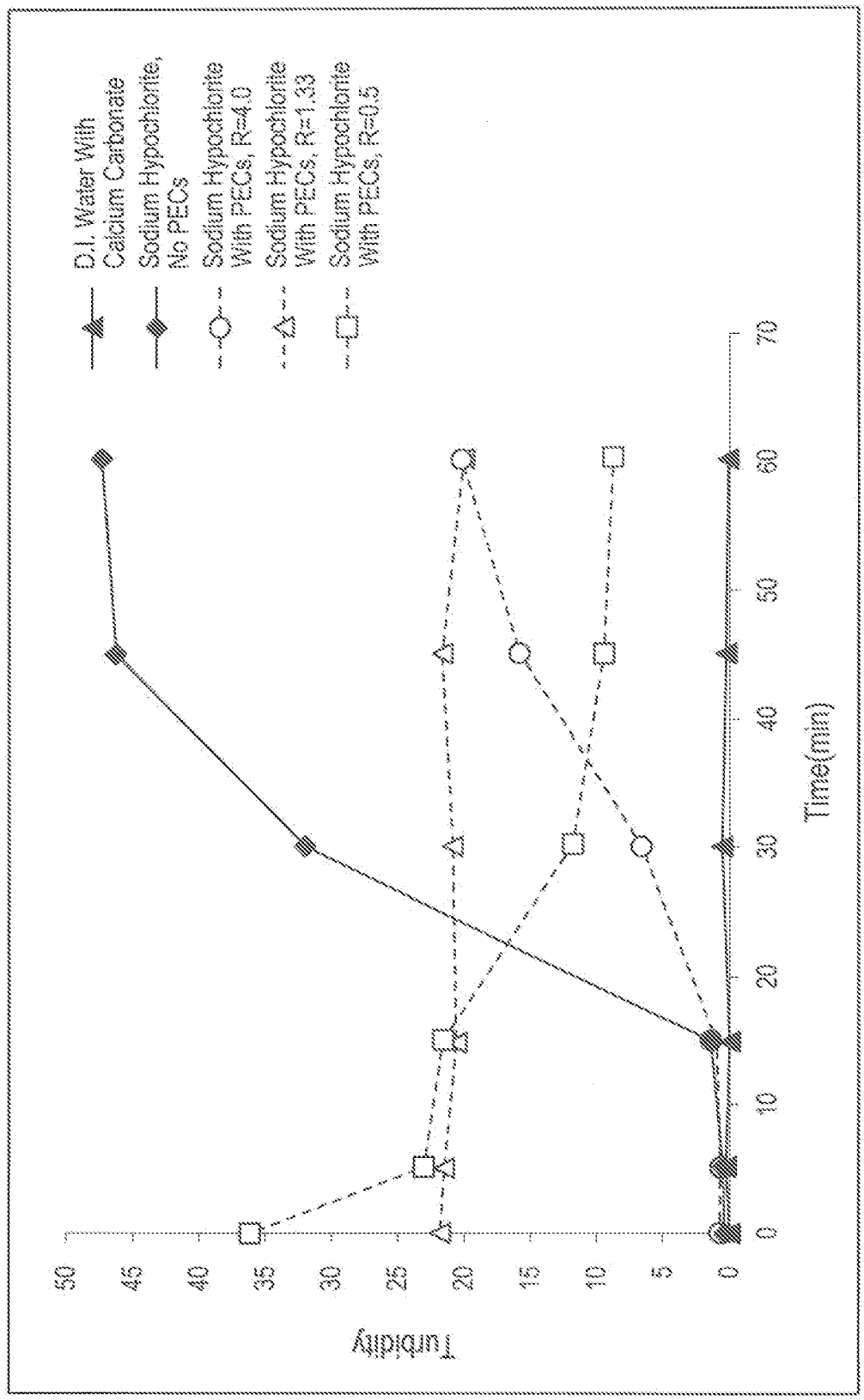

PRECURSOR POLYELECTROLYTE COMPLEXES COMPOSITIONS COMPRISING OXIDANTS

CROSS-REFERENCE TO RELATED APPLICATIONS

The present application is a continuation-in-part of copending U.S. patent application Ser. No. 12/749,288, filed Mar. 29, 2010, and U.S. patent application Ser. No. 13/046,385, filed Mar. 11, 2011. The disclosure of each of the above applications is incorporated by reference in its entirety.

BACKGROUND OF THE INVENTION

1. The Field of the Invention

The present invention relates to polyelectrolyte complexes ("PECs"), their precursor compositions, and methods of making and using such compositions.

2. Description of Related Art

Consumers desire cleaning products that deliver additional benefits, e.g., that stay cleaner longer, inhibit the growth of microbes, maintain appearance, etc., all without the additional effort of a separate treatment step in addition to regular cleaning.

Modification of household surfaces, both hard and soft, can provide many benefits. It is important that such modifications be reversible, and hence, do not involve the formation of permanent covalent bonds between the materials employed in the treatment.

It is also desirable that the modification be achieved via thin layers not apparent to the unaided eye in order to minimize effort needed to achieve modification and to minimize any undesirable aesthetic changes in the appearance of surfaces.

In healthcare, there is a continuing desire to reduce hospital acquired infections. Modification of surfaces achieved with a minimum of effort to reduce microbial contamination is a recognized area of interest. Related to this goal is the desire to reduce transmission of diseases from surface-borne microbial pathogens present in public places, including buildings and vehicles.

As in healthcare, removing and controlling the growth of microbes such as bacteria and fungi is important in many industrial processes. Controlling microbe growth and achieving microbe removal from surfaces affects productivity, practicality, and profitability of the process. For example, bacterial fouling of heat exchanger surfaces, fouling of web formation and handling equipment in the production or recycling of paper, and similar fouling in the processing of biomass, etc. can have a large negative impact. Modification of the surfaces involved, control of the surface properties of the microbes involved, or both can be used to prevent or minimize microbial fouling and/or to enable the efficient removal of microbial organisms from such processes.

Many commercial disinfectants employing typical quaternary ammonium biocides deposited on surfaces to reduce microbial loads tend to leave the treated surfaces sticky to the touch, which attracts dust and detritus. This leads to unsightly surfaces that require frequent cleaning and reapplication of the biocide in order to remain effective.

There is a need for concentrated compositions capable of providing stable, but thin and substantially invisible layers or particles over a surface to be treated so as to provide enhanced surface protective properties such as reduced adhesion of soil, reduced biological and environmental contamination, and the ability to kill microbes that are deposited onto the surfaces in a variety of ways (e.g., through airborne contaminants, food preparation, direct epidermal contact, exposure to bodily fluids, etc.). It would be a further advantage for such compositions to simultaneously clean and treat the surfaces to which they are applied so that separate cleaning and treatment steps are not required.

BRIEF SUMMARY OF THE INVENTION

In one aspect, the present invention is directed to a composition comprising a water-soluble first polyelectrolyte bearing a net cationic charge or capable of developing a net cationic charge, and a water-soluble second polyelectrolyte bearing a net anionic charge or capable of developing a net anionic charge. The total polyelectrolyte concentration of the composition is at least 110 millimolar, and the composition is free of coacervates, precipitates, latex particles, synthetic block copolymers, silicone copolymers, cross-linked poly(acrylic) and cross-linked water-soluble polyelectrolyte.

Another embodiment of the present invention is directed to a composition comprising an oxidant (e.g., an alkali or alkaline earth hypohalite), a polyelectrolyte precursor composition comprising a water-soluble first polyelectrolyte bearing a net cationic charge or capable of developing a net cationic charge, and a water-soluble second polyelectrolyte bearing a net anionic charge or capable of developing a net anionic charge. The total polyelectrolyte concentration of the composition is at least 110 millimolar, and the composition is free of coacervates, precipitates, latex particles, synthetic block copolymers, silicone copolymers, cross-linked poly(acrylic) and cross-linked water-soluble polyelectrolyte.

Another embodiment of the present invention is directed to an aqueous composition consisting essentially of water, a water-soluble first polyelectrolyte bearing a net cationic charge or capable of developing a net cationic charge, a water-soluble second polyelectrolyte bearing a net anionic charge or capable of developing a net anionic charge, optionally, one or more of an oxidant, electrolyte, surfactant, solvent, antimicrobial agent, buffer, or any combination thereof. Additionally, the composition may optionally include stain and soil repellants, lubricants, odor control agents, perfumes, fragrances, fragrance release agents, bleaching agents, acids, bases, dyes and/or colorants, solubilizing materials, stabilizers, thickeners, defoamers, hydrotropes, cloud point modifiers, preservatives, other polymers, and combinations thereof. The total polyelectrolyte concentration of the composition is at least 110 millimolar, and the composition is free of coacervates, precipitates, latex particles, synthetic block copolymers, silicone copolymers, cross-linked poly(acrylic) and cross-linked water-soluble polyelectrolyte.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which:

FIG. 1 plots turbidity data of the compositions of Example 14 over time.

DETAILED DESCRIPTION OF THE PREFERRED EMBODIMENTS

I. Definitions

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

The term water-soluble polymer as used herein means a polymer which gives an optically clear solution free of precipitates at a concentration of 0.001 grams per 100 grams of water, preferably 0.01 grams/100 grams of water, more preferably 0.1 grams/100 grams of water, and even more preferably 1 gram or more per 100 grams of water, at 25° C.

As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." The term "disinfect" may generally refer to the elimination of many or all pathogenic microorganisms on surfaces with the exception of bacterial endospores. The term "sterilize" may refer to the complete elimination or destruction of all forms of microbial life and which is authorized under the applicable regulatory laws to make legal claims as a "sterilant" or to have sterilizing properties or qualities.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("wt %'s") are in wt % (based on 100 weight % active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting that 1.0 wt % corresponds to 10,000 ppm.

II. Introduction

According to an embodiment, the PEC precursor solutions of the present invention comprise a water-soluble first polyelectrolyte having a cationic charge or capable of developing a cationic charge, and a second water-soluble polyelectrolyte having an anionic charge or capable of developing an anionic charge wherein the total polyelectrolyte concentration of the solution is at least 110 millimolar (mM). The solution is advantageously free of coacervates, precipitates, latex particles, block copolymers, silicone copolymers, cross-linked poly(acrylic), and cross-linked water-soluble polyelectrolytes. The PEC precursor solutions may be single phase, clear or slightly colored transparent (e.g., bluish) solutions without the presence of precipitated particles, suspended solids, flocculates, or other large aggregates that would cause a hazy or milky appearance.

According to another embodiment, the polyelectrolytes are not selected from the group consisting of polymeric fluorosurfactant derived from polymerization of a fluorinated oxetane, silicone polymer, anionic latex, cationic latex, mixtures of polyelectrolytes and a non-polymeric material (crosslinker) capable of reacting with the polyelectrolytes to form covalent bonds which crosslink the polyelectrolytes, anionic polysaccharide containing glucoronic acid, N-acyl-chitosan with an $C_1$-$C_{12}$ alkyl group, and/or combinations thereof.

Although there are a variety of materials available that are already surface modified for a specific purpose, there is also a large installed base of relatively ordinary materials, which surfaces would benefit from simple, non-permanent, and invisible modification.

PECs formed through dilution of the present PEC precursor compositions can provide modification of such surfaces, anchoring of antimicrobial materials to surfaces etc., and can function without forming macroscopic films. In other words, they may function through adsorption onto surfaces on a molecular scale, with the adsorbed layers having dimensions on the order of nanometers. Such adsorbed layers are generally invisible to the unaided eye, and do not rely on the formation of permanent chemical bonds between the polymers and the surface, but instead on a combination of electrostatic and hydrophobic interactions with the surface.

Solutions of PECs that are active at solid surfaces yet stable during the course of use can be produced via methods taught in US2011/0236582 (U.S. patent application Ser. No. 12/749,288, incorporated by reference above in the priority claim). In one embodiment, the PEC solutions produced via such methods may deliver PECs at concentrations (measured as the total concentration of charged associating groups) of about 100 mM or less.

However, in some applications it may be inconvenient to utilize ready to use PEC solutions, that is, in order to deliver PEC solutions to some surfaces in a variety of applications, it would be preferable to use a concentrate which can be easily diluted, preferably with a safe solvent such as water, at or before time of use. Applicants have thus investigated compositions and means of producing relatively concentrated "PEC precursor" solutions. Such precursor compositions, which may or may not comprise PECs themselves, produce PEC solutions upon mixing and/or dilution. The PECs in these diluted compositions can then produce the desired modification of both inanimate and animate surfaces.

Surprisingly, although aqueous mixtures of polyelectrolytes of opposite charge may exhibit the undesirable formation of precipitates instead of soluble complexes at total polymer concentrations of 50 mM or 100 mM, the inventors have found that it is possible to prepare clear solutions of the mixed polyelectrolytes at concentrations of at least 110 mM, at least 120 mM, and of at least 130 mM. This characteristic also exists at much higher concentrations, such as at least 500 mM or even at least 1000 mM. In other embodiments, the other concentration ranges may include, but not limited to, about 120 mM to about 200 mM, about 130 mM to about 200 mM, about 200 mM to about 400 mM, about 200 mM to about 1,000 mM, about 500 mM to about 1,000 mM, about 300 mM to about 1,000 mM, about 400 mM to about 1,000 mM, about 500 mM to about 2,000 mM, about 500 mM to about 3,000 mM, about 200 mM to about 3,000 mM, about 1,000 mM to about 3,000 mM, about 1,500 mM to about 3,000 mM. Also surprisingly, the dilution of these concentrated (PEC precursor solutions by very large factors, e.g. often 100× or more, yields stable solutions comprising PECs. This is achieved without any special need for high energy or high shear mixing conditions. The stable PEC particles exhibit dimensions consistent with colloidal solutions, that is, diameters of about 500 nm or less. The stable PEC particles do not flocculate or aggregate into larger particles which may settle out of solution, or that would cause a hazy or milky appearance in the absence of any adjuvants which might be present as particles, such as abrasives, beads, flakes, opacifiers, etc. that may be added. Furthermore, PEC solutions produced via dilution of the PEC precursor solutions may be clear to slightly transparently colored (e.g., blue) in appearance, with an absence of precipitates or coacervates readily detectable by the unaided eye.

The PEC precursor compositions yield solutions comprising stable PECs when they are diluted with appropriate solvents or solutions containing appropriate adjuvants as described herein. Without being bound by theory, applicants believe that control of the interactions between soluble polyelectrolytes in the precursor solutions ensures delivery of truly soluble polyelectrolytes upon dilution, which in turn allows the assembly of the PECs via molecular scale interactions between oppositely charged groups on two or more polyelectrolytes. As a result, it is believed that the polymers relax into preferred conformations quickly, without the formation of large precipitates, thus ensuring the production of stable PECs of the desired size and composition. Thus, the dilution of PEC precursor solutions to provide stable PECs in solution eliminates the dependence of PEC formation on the input of large amounts of energy through high shear mixing or other high energy input as taught in other art. Similarly, there is no need to recover or remove PEC coacervate or precipitate particles or coagulates from the solutions in which they are formed prior to use.

In another aspect of the present invention, the PEC precursor solutions, when diluted with water or an aqueous solvent mixture, yield stable solutions of PECs. The PECs are characterized as having diameters less than about 500 nm, preferably less than 200 nm, and even more preferably less than 100 nm.

In another aspect of the invention, the PECs formed by dilution of a PEC precursor solution modify a solid surface via non-covalent interactions with the surface, providing one or more benefits selected from hydrophilic surface modification, hydrophobic surface modification, extended antimicrobial activity of the surface, reduced fouling of the surface by microorganisms, reduced adhesion of microorganisms to the surface, stays cleaner longer or easier to clean next time.

In another aspect of the present invention, the PEC precursor solutions, including any optional adjuvants, comprise a first solution which is held in a first chamber of a dual chamber package, for example, a dual chamber bottle. A second solution comprising a solvent and optionally comprising other adjuvants may be held in a second chamber of the package. The contents of the two chambers of the package may be mixed at the time of use (for example, through the use of a trigger sprayer with dual dip tubes) to provide a solution of PECs and optional adjuvants.

In an embodiment, the present invention provides PEC precursor compositions that produce stable polyelectrolyte complexes upon dilution with an aqueous solvent.

In an embodiment, the present invention provides PEC precursor compositions which are compatible with the presence of surfactants, biocides and oxidants.

In an embodiment, the present invention provides PEC precursor compositions which, upon dilution, provide PECs that result in the modification of inanimate surfaces and deliver benefits such as reduced microbial fouling, reduced microbial surface loads, easier subsequent cleaning, simultaneous cleaning and surface treatment, reduced adhesion of oily soils, reduced spotting due to evaporation of water or other volatile components, all without the need for permanent chemical bonds between the PECs and the surfaces, and without the need for the formation of a macroscopic film, that is, by adsorbed layers of PECs that are invisible to the unaided eye.

In an embodiment, the present invention provides PEC precursor compositions that eliminate the need for storage of PEC solutions by providing the formation of PECs on-demand through a simple dilution step which can be achieved through simple manual dilution, an automated dilution and delivery system, or a package design convenient for use by consumers or professionals.

In an embodiment, the present invention provides PEC precursor compositions which, upon dilution, provide PECs that can modify the surfaces of animate objects, such as insects, crop leaves or seeds, or the surfaces of microbial organisms, (e.g., bacteria, viruses, bacterial spores, or fungal spores). Modification of microbe surfaces via the adsorption of PECs can provide a change in the electrical charge of the microbes which can then be used for the manipulation or inactivation of them in a variety of ways. For example, control of surface characteristics of certain microbes, such as bacterial or fungal spores, may be useful in collection, isolation, identification, or adhesion of such spores.

The aqueous PEC precursor solutions may optionally comprise an adjuvant selected from—an inorganic acid or base, an organic acid or base, a salt of the inorganic acid or base, a salt of the organic acid or base, a buffering agent, an oxidant, a surfactant, or a water-miscible solvent. The precursor solutions themselves may or may not comprise PECs. Where they do not comprise PECs, they instead comprise the polyelectrolytes in a soluble state that will assemble to form the PECs upon dilution, i.e., the precursor solutions are stable, one phase aqueous fluids free of precipitates or macroscopic aggregates that may otherwise form due to interactions between the polyelectrolytes. Subsequent addition of other adjuvants such as abrasives, opacifiers, etc. may of course yield a more hazy or milky appearance.

The presence of PECs and their dimensions in aqueous solutions may be characterized via static or dynamic light scattering (DLS). It is well known to those skilled in the art that light scattering analyses need to be conducted with an optimum concentration of scattering particles (PECs, for example). The concentration of polyelectrolytes in many of the PEC precursor solutions is often too high for meaningful DLS analyses. However, dilution of the PEC precursor solution to form the PECs of interest usually results in solutions which are amenable to analysis by DLS, and hence examples below will demonstrate that stable PECs (generally, having diameters less than 500, preferably less than 200, and more preferably less than 100 nm) are formed upon dilution of the precursor solutions.

A convenient way to express compositional characteristics of the PEC composition and precursor is through the value of "R" (described below) which characterizes the charge on the PECs to be formed, and by the desired dilution factor. The dilution factor can be adjusted over a wide range, depending on the method of dilution to be used. For example, if the PEC precursor solutions are to be diluted through use of a consumer-friendly dual-chamber bottle equipped with a trigger sprayer, the viscosity of the PECs precursor solutions must be sufficiently low so as to not affect the performance of the package. Alternatively, if the PEC precursor solutions are to be diluted by a user via pouring into ordinary tap water (or vice versa), with or without a calibrated dispensing aid such as a bottle cap, the viscosity of the precursor solution would be less important and could be adjusted to an desired target. As another alternative, the PEC precursor solutions may comprise one liquid stream which is combined with a second liquid stream and ordinary water in an apparatus designed to produce treatment, cleaning or disinfecting solutions for use by janitorial personnel.

In another alternative, if the PEC precursor solutions comprise a concentrated oxidant as an adjuvant, such as sodium hypochlorite at about 1% to about 10% by weight, the dilution of the precursor solution may be achieved by the consumer with ordinary tap water through pouring into a washing machine, adding the precursor to an automated dispenser incorporated into a washing machine, or by pouring the precursor into a vessel containing ordinary tap water.

Aqueous solutions of the anionic and cationic polyelectrolyte stocks that are to be blended to produce the PEC precursor solutions can be prepared in any manner with conventional equipment, including dissolution of solid polymers in the aqueous solutions, dilution of a neat polymer melt directly after completion of polymerization via any conventional means, or dilution of a solution of the polymer obtained after polymerization in which the polymerization solvent or solvents are miscible with the aqueous solutions. Most convenient may be the direct use of polyelectrolyte solutions in aqueous solvents supplied by polymer manufacturers in which the polymer solids level is adjusted such that the resulting viscosity of the polyelectrolyte is convenient for conventional liquid handling systems.

In at least some embodiments, the present invention does not contemplate the use of so-called water-dispersable polyelectrolytes, since it is believed that a significant fraction of the ionic groups present in "water-dispersible" polymers or polyelectrolytes may not be readily accessible to the oppositely charged ionic groups of another polymer. If some fraction of the ionic groups of the water-dispersible polymers are hidden or occluded within a hydrophobic region of the polymer, or the polymer itself adopts a given microstructure in a diluent such as water, the assembly conditions of the PECs during dilution are not controlled, and the nature of the PECs produced cannot be controlled. For essentially the same reasons, at least some embodiments of the present invention do not contemplate the use of latex particles of any kind.

In at least some embodiments, the present invention does not contemplate the use of synthetic block copolymers that can form complex coacervate micelles. It is believed that complex coacervate micelles, sometimes referred to as polymeric micelles, are characterized by restriction of the charged groups of the polymers to a complex domain that is formed by the coacervate core, and a corona surrounding the core formed by a hydrophilic and neutral block on at least one of the polymers. Stable complex coacervate micelles are only formed if the length of the ionic block, the length of the hydrophilic block, and the length of the neutral block on the block polymer are appropriate. The formation of such structures is believed to be an undesirable competitive process to the formation of the PECs formed by the dilution of precursor solutions as described herein. The PECs of the present invention do not require the presence of a hydrophilic and neutral block.

The lack of charged groups on the exterior of the complex coacervate micelles is a further limitation, since interactions between the charged groups of one or both polymers with adjuvants such as surfactants, germicidal quaternary ammonium compounds, or soluble metal ions is not possible due to the requirement of a neutral hydrophilic block present in the corona of the complex coacervate micelles. The PECs of the present invention, in contrast, when formed by dilution from precursor solutions, may interact with adjuvants, as desired by the particular application.

Random copolymers of a wide range are quite acceptable for use in the present invention, as long as they exhibit the appropriate solubility.

The PEC precursor solutions may be made by blending aqueous solutions of at least one water-soluble polyelectrolyte having a cationic charge or capable of developing a cationic charge, with an aqueous solution of at least one water-soluble polyelectrolyte having an anionic charge, or capable of developing an anionic charge via conventional mixing equipment. For example, a batch tank equipped with an agitator, or pumping through a static mixer may be employed.

The water-soluble polyelectrolytes are typically in soluble form prior to this mixing step so that they will form clear solutions in water at a concentration of at least 0.1 gram polymer/100 grams of water, preferably 1 gram polymer/100 grams of water, preferably at least 10 grams polymer/100 grams water, or more preferably in excess of 50 grams polymer/100 grams of water at 25° C. In the case of some polymers, an appropriate salt may be formed in order to achieve water solubility, and thus a pre-formed salt of the polymer in water may be used or a polymer may be dissolved in water containing an appropriate acid or base which forms the water-soluble salt of the polymer.

For example, chitosan is a natural polymer capable of developing a cationic charge and exhibits acceptable solubility in water when it is dissolved in water containing an acid, such as citric or acetic acid. Thus, an acid may be present as an adjuvant in the chitosan solution used in the formation of PEC precursor solutions. The amount of acid required may be readily determined by the concentration of the chitosan desired, and by the appearance of the precursor solution formed with an anionic polymer. If the blending of the chitosan with the anionic polymer results a precursor solution at the desired "R" value having a cloudy appearance, then additional acid may be required, either added to the chitosan stock solution, the anionic polymer solution, or both, in order to ensure that the final PEC precursor solution remains free of precipitates. Alternatively, a solid salt of chitosan, such as the pyrrolidone carboxylic acid salt of chitosan, may be dissolved directly in water and used.

There are no particular restrictions on the order of addition of the polyelectrolytes. The agitation needed may depend on the viscosity of the polyelectrolyte solutions, but since macroscopic aggregates due to precipitation of the polymers are to be avoided, the mechanical energy input may be limited to, and determined by, whatever input is needed to ensure complete blending of the two polymer solutions, not by any need for shear-induced destruction of any macroscopic colloidal aggregates. Thus, in many examples, the maximum practical concentration of the polyelectrolytes in the precursor solutions may be limited by the solubility of the individual polyelectrolyte solution stocks, or the viscosity of the resultant clear, one phase precursor solution, strictly for mechanical reasons. In general, PEC precursor solutions, in the absence of particulate adjuvants, will exhibit bulk viscosities less than about 1 million centipoise, preferably less than about 10,000 centipoise, more preferably less than about 1,000 centipoise.

There are no particular restrictions on the relative molecular weights of the cationic and anionic polyelectrolytes in the PEC precursor solutions, contrary to what is taught elsewhere in the art. This is because the PECs are assembled via dilution with a second aqueous solvent which may include optional additives. In other words, the precursor solutions contain soluble polymers but do not necessarily have to contain stable PECs themselves.

A convenient way to express the composition of the PEC precursor solutions and the PECs formed upon dilution of the precursor solutions is to calculate the ratio of the moles or number of cationic charges to corresponding moles or number of anionic charges present in the solution, based on the relative amounts of the polymers added to the bulk solution. Herein below, the parameter "R" is used to denote the molar ratio of cationic (or potentially cationic) groups to that of anionic (or potentially anionic). groups of the two respective polyelectrolytes comprising the associative PECs of the present invention, where accordingly:

$$R=Q^+/Q^-$$

where $Q^+$ is the number of moles of cationic charges, $Q^-$ is the number or moles of anionic charges; wherein $$Q^+=(C_{cationic})*(F_{cationic})*(Q_{cationic})/(M_{cationic})$$

where $C_{cationic}$ is the concentration of cationic polymer in weight percent, $F_{cationic}$ is the weight fraction cationic monomer in total cationic polymer weight, thus being between 0 and 1, $Q_{cationic}$ is the number of charges per cationic monomer unit, $M_{cationic}$ is the molecular weight of the monomer unit in polymerized form. Correspondingly:

$$Q^-=(C_{anionic})*(F_{anionic})*(Q_{anionic})/(M_{anionic})$$

where $C_{anionic}$ is the concentration of anionic polymer in weight percent, $F_{anionic}$ is the weight fraction anionic monomer in total anionic polymer weight, thus being between 0 and 1, $Q_{anionic}$ is the number of charges per anionic monomer unit, and $M_{anionic}$ is the molecular weight of the monomer unit in polymerized form.

It should be noted that, in the case of polymers comprising multiple cationic (or potentially cationic) or multiple anionic (or potentially anionic) groups, the corresponding Q parameter ($Q^+$ or $Q^-$) would be calculated as a sum of the individual Q values of the same charge.

In the case of so-called amphoteric copolymers, which contain both cationic (or potentially cationic) and anionic (or potentially anionic) groups, a single polymer would contribute to both the total $Q^+$ and $Q^-$ parameters. Of course, in the case of amphoteric polymers, formation of a PEC as described herein would still require the presence of a first amphoteric polymer with a given net charge, for example, cationic, and a second amphoteric polymer with a given net charge, or that is capable of developing a net charge, which is opposite to that of the first amphoteric polymer.

The R values of the PEC precursor solutions may generally be the same as that of the PECs which are made through the dilution process, i.e., between about 0.1 and 20.

The PEC precursor solutions may employ water as a solvent. Additional water-miscible solvents such as lower alcohols, glycols, glycol ethers, glycol esters, dimethyl sulfoxide, dimethyl formamide, and the like may be employed. Other liquid materials, such as hydrocarbons, oils, etc., which are not miscible with water at a concentration of at least 1 gram liquid/100 grams of water at 25° C. may not be considered as components of the solvent system in water-based solvent embodiments. That said, such materials may of course be included in the aqueous solutions through the use of surfactants or the addition of certain water-miscible solvents serving as "coupling agents".

Selection of adjuvants for incorporation into the precursor solutions may depend on the target R value of the PECs to be produced from the PEC precursor solutions, as well as on the type of adjuvants present in the aqueous solution to be used in the dilution of the precursor solutions. Selection should ensure the polyelectrolytes are soluble and thus able to assemble into PECs in the final diluted solution. A general example of adjuvant selection was given above where chitosan was selected as the cationic polyelectrolyte. By way of other general examples, and prior to a discussion of specific PEC precursor solutions, the following principles have also been discovered.

In the case of anionic polyelectrolytes in which the anionic moieties are carboxylic acids, the anionic polyelectrolyte solution may be prepared from the polyelectrolyte in the acid form, i.e, the acid groups are in the protonated or non-ionized form or are substantially in the acid form. In other words, the pH of the anionic polyelectrolyte solution prior to mixing with the cationic polyelectrolyte solution is at or below the pKa (or estimated pKa) of the acid groups of the anionic polyelectrolyte, or at or below about pH 4 in the absence of information about the pKa. If the pH of the anionic polyelectrolyte solution requires adjustment (e.g., due to minor impurities or method of polymerization of the anionic polyelectrolyte), sufficient amounts of an appropriate acid or base may be added.

In the case of anionic polyelectrolytes in which the anionic moieties are carboxylic acids which are present in the ionized (salt) form, the pH of the polyelectrolyte solution prior to mixing with the cationic polyelectrolyte solution may be adjusted to near or below the pKa (or estimated pKa or about pH 4 in the absence of information about the pKa.) of the acid groups of the anionic polyelectrolyte via the addition of an effective amount of an appropriate acid or base.

In the case of anionic polyelectrolytes in which the anionic moieties are carboxylic acids which are present (or in which some fraction of the moieties are present) in the ionized (salt) form, an appropriate electrolyte may be added to the anionic polyelectrolyte solution in an amount sufficient to produce a clear precursor solution when the anionic polyelectrolyte solution is mixed with the cationic polyelectrolyte solution.

In the case of anionic polyelectrolytes in which the anionic moieties are carboxylic acids which are present (or in which some fraction of the moieties are present) in the ionized (salt) form, an appropriate electrolyte may be added to the cationic polyelectrolyte solution in an amount sufficient to produce a clear precursor solution when the anionic polyelectrolyte solution is mixed with the cationic polyelectrolyte solution.

In the case of anionic polyelectrolytes in which the anionic moieties are carboxylic acids which are present (or in which some fraction of the moieties are present) in the ionized (salt) form, an appropriate electrolyte may be added to both the cationic polyelectrolyte solution and the anionic polyelectrolyte solution in an amount sufficient to produce a clear precursor solution when the polyelectrolyte solutions are mixed.

In the case of anionic polyelectrolytes comprising anionic moieties that are not carboxylic acids or comprising mixtures of anionic moieties including carboxylic acids and non-carboxylic acid anionic moieties, and in which the pH of the anionic polyelectrolyte solution may not be adjusted below the pKa or estimated pKa of one or more of the anionic moieties or pH about 4, or in the case in which the desired pH of the anionic polyelectrolyte solution is significantly above the pKa or estimated pKa of the anionic moieties, an appropriate electrolyte may be added to the anionic polyelectrolyte solution in an amount sufficient to produce a clear precursor solution when the polyelectrolyte solutions are mixed.

The "electrolyte" mentioned may be selected from a wide range of compounds, including organic acids and bases, inorganic acids or bases, their water-soluble salts, or combinations thereof. In an embodiment, the electrolyte may be an alkali metal salt of hypochlorous acid, alkaline metal salt of hypochlorous acid, or combinations thereof (e.g., sodium hypochlorite, calcium hypochlorite, or combinations thereof). An electrolyte will be deemed appropriate when its use is indifferent to, or known to be compatible with, other adjuvants which may be present in the final solution of the PECs produced via dilution of the PEC precursor solutions.

III. Suitable Synthetic Polymers

The polymers may be homopolymers or copolymers, and they may be linear or branched. Copolymers may be synthesized by processes expected to lead to statistically random or so-called gradient type copolymers. In contrast, water-soluble block copolymers are not suitable suitable for use, since these types of polymers may form aggregates or micelles, in which the more hydrophobic block(s) comprise the core of the aggregate or micelles and the more hydrophilic block(s) comprise a "corona" region in contact with water. It is believed that these self-assembly processes undesirably compete with the formation of PECs.

Although mixtures of water-soluble polymers may be suitable for use, the mixtures selected should not comprise block copolymers capable of forming so-called "complex coacervate" micelles through self-assembly. When the polymers are copolymers, the ratio of the two or more monomers may vary over a wide range, as long as water solubility of the polymer is maintained.

Examples of cationic monomers that may be used include, but are not limited to diallyldimethyl ammonium chloride, quaternary ammonium salts of acrylamides, quaternized derivatives of acrylate esters and amides—etc. Monomers capable of developing a cationic charge include ethyleneimine and its derivatives, vinyl imidazole, vinyl pyridine oxide, etc. Combinations of any of the foregoing may also be used.

Additional suitable cationic polymers include homopolymers or copolymers of monomers having a permanent cationic charge or monomers capable of forming a cationic charge in solution upon protonation. Examples of permanently cationic monomers include, but are not limited to, diallyl dimethyl ammonium salts (such as the chloride salt, referred to herein as DADMAC) quaternary ammonium salts of substituted acrylamide, methacrylamide, acrylate and methacrylate, such as trimethylammoniumethyl methacrylate, trimethylammoniumpropyl methacrylamide, trimethylammoniumethyl methacrylate, trimethylammoniumpropyl acrylamide, 2-vinyl N-alkyl quaternary pyridinium, 4-vinyl N-alkyl quaternary pyridinium, 4-vinylbenzyltrialkylammonium, 2-vinyl piperidinium, 4-vinyl piperidinium, 3-alkyl 1-vinyl imidazolium, and the ionene class of internal cationic monomers. The counterion of the cationic co-monomer can be selected from, for example, chloride, bromide, iodide, hydroxide, phosphate, sulfate, hydrosulfate, ethyl sulfate, methyl sulfate, formate, and acetate.

Examples of monomers that are cationic on protonation include, but are not limited to, acrylamide, N,N-dimethylacrylamide, N,N di-isopropylacryalmide, N-vinylimidazole, N-vinylpyrrolidone, vinyl pyridine N-oxide, ethyleneimine, dimethylaminohydroxypropyl diethylenetriamine, dimethylaminoethyl methacrylate, dimethylaminopropyl methacrylamide, dimethylaminoethyl acrylate, dimethylaminopropyl acrylamide, 2-vinyl pyridine, 4-vinyl pyridine, 2-vinyl piperidine, 4-vinylpiperidine, vinyl amine, diallylamine, methyldiallylamine, vinyl oxazolidone; vinyl methyoxazolidone, and vinyl caprolactam.

Monomers that are cationic on protonation typically contain a positive charge over a portion of the pH range of 2-11. Cationic polymers may also include other monomers, for example monomers having an uncharged hydrophilic or hydrophobic group. Suitable copolymers contain acrylamide, methacrylamide and substituted acrylamides and methacrylamides, acrylic and methacrylic acid and esters thereof.

The cationic polymer level in the compositions of the present invention may typically range from about 0.001 wt % to about 5.0 wt %, or from about 0.01 wt % to about 2.5 wt %, or from about 0.01 wt % to about 1.0 wt %, or from about 0.1 wt % to about 0.50 wt %.

Examples of anionic monomers that may be used include, but are not limited to acrylic acid, methacrylic acid, crotonic acid, maleic acid, etc. Phthalic acid and its isomers (e.g., including acid-terminated polyesters or condensates of polyesters, polyurethanes or polyamides and ethylene, propylene or butylene oxide, etc) may also be suitable for use. Sulfonate functional monomers such as acrylamidopropyl methane sulfonic acid (AMPS) and the like may also be employed. Combinations of any of the foregoing may also be used.

Additional suitable anionic polymers include, but are not limited to, polycarboxylate polymers and copolymers of acrylic acid and maleic anhydride, or alkali metal salts thereof, such as the sodium and potassium salts. Suitable are copolymers of acrylic acid or methacrylic acid with vinyl ethers, such as, for example, vinyl methyl ether, vinyl esters, ethylene, propylene and styrene. Also suitable are polymers containing monomers capable of taking on an anionic charge in aqueous solutions when dissolved in water that has been adjusted to an appropriate pH using an acid, a base a buffer or combination thereof. Examples include, but are not limited to, acrylic acid, maleic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, and sulfoethyl acrylate. Suitable acid monomers also include styrenesulfonic acid, acrylamide methyl propane sulfonic acid, 2-methacryloyloxy-methane-1-sulfonic acid, 3-methacryloyloxy-propane-1-sulfonic acid, 3-(vinyloxy)-propane-1-sulfonic acid, ethylenesulfonic acid, vinyl sulfuric acid, 4-vinylphenyl sulfuric acid, ethylene phosphonic acid and vinyl phosphoric acid. Examples of commercially available products are Sokalan CP5 and PA30 from BASF, ALCOSPERSE 175 and 177 from Alco and LMW 45N and SPO2N from Norsohaas. Also suitable are natural anionic polymers, including but not limited to saccharinic gums such as alginates, xanthates, pectins, carrageenans, guar, carboxymethyl cellulose, and scleroglucans.

The anionic polymer level in the compositions of the present invention may typically range from about 0.001 wt % to about 5.0 wt %, or from about 0.01 wt % to about 2.5 wt %, or from about 0.01 wt % to about 1.0 wt %, or from about 0.1 wt % to about 0.50 wt %.

Amphoteric polymers derived from the copolymerization of one or more of a cationic and an anionic monomer, with or without the presence of a third monomer incapable of developing a charge (nonionic monomers) may similarly be employed. Examples of nonionic monomers include, but are not limited to, acrylamide, dimethylacrylamide and other alkyl acrylamides which have not been "quaternized" e.g., ethylene, propylene and/or butylene oxide.

One or both of the polyelectrolytes may be natural or derived from natural sources, such as chitosan, quaternized guar, cationically modified starches or celluloses. Anionically charged natural or naturally derived polymers include alginate salts, inulin derivatives, anionically modified starches, etc.

The random copolymers may comprise one or more monomers bearing the same charge or capable of developing the same charge and one or more monomers which are nonionic, i.e, not capable of bearing a charge. Copolymers may be synthesized by graft processes, resulting in "comb-like" structures.

Preferred copolymers include so-called "hybrid" materials from Akzo Nobel such as Alcoguard H 5240. These materials are described as comprising polysaccharides and synthetic monomers which can function in the same manner as acrylate/maleate copolymers (i.e., a water-soluble polymer with anionically charged groups) in cleaning formulations.

Water-soluble copolymers derived from a synthetic monomer or monomers that may be chain terminated with a hydroxyl-containing natural material, such as a polysaccharide, are preferred. Such materials may be synthesized with ordinary free-radical initiators.

IV. Adjuvants

Surfactants of all types can be used. Where the sustainability of the formulations are of concern, surfactants derived from natural or sustainable sources are preferred.

A. Buffers & Electrolytes

Buffers, buffering agents and pH adjusting agents, when used, include, but are not limited to, organic acids, mineral acids, alkali metal and alkaline earth salts of silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2-methylpropanol. In one embodiment, preferred buffering agents include but are not limited to; dicarboxlic acids, such as, succinic acid and glutaric acid. Some suitable nitrogen-containing buffering agents are amino acids such as lysine or lower alcohol amines like mono-, di-, and tri-ethanolamine. Other nitrogen-containing buffering agents are Tri(hydroxymethyl)amino methane $(HOCH_2)_3CNH_3$ (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis (methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, and acetic acid. Mixtures of any of the above may also be acceptable. Useful inorganic buffers/alkalinity sources include ammonia, the alkali metal carbonates and alkali metal phosphates, e.g., sodium carbonate, sodium polyphosphate.

In one embodiment, when a hypohalous acid (e.g., hypochlorous acid) is used, an acid may be beneficial to stabilize the pH and maintain the desired ratio of hypochlorous acid to hypochlorite anion. In some cases, the acid may be added to a solution containing hypochlorite anion to convert this anion to hypochlorous acid. An acid may also be used to control the formation of chlorine dioxide from a chlorite salt. Acid may also be used with peroxygen compounds to control stability or reactivity. Acids may also be added for cleaning and removal of soils such as hard water deposits and rust. Exemplary acids include, but are not limited to inorganic acids such as hydrochloric acid or sulfuric acid; and organic acids such as sulfonic acid, polysulfonic acid, monocarboxylic acid, dicarboxylic acid, polycarboxylic acid, acid sulfate, acid phosphate, phosphonic acid, aminocarboxylic acid and mixtures thereof. Specific examples of acids, include but are not limited to, acetic acid, succinic acid, glutaric acid, adipic acid, polyacrylic acid, sodium bisulfate, 3-pyridine sulfonic acid, dodecyl benzene sulfonic acid, polyacrylic acid, and mixtures thereof. Sodium, potassium and any other salt of any of these acids or mixtures thereof may also be included to achieve the desired pH and create a buffer system that resists changes in pH.

Buffers and electrolytes "screen" the interactions between the polyelectrolytes of the present invention, and thus may be used to modify phase behavior, such as preparing formulations "close" to a coacervate phase boundary, which may be useful where the complexes become sufficiently large (up to about 500 nm diameter) or high enough in total molecular weight to exhibit enhanced adsorption onto surfaces. Any suitable electrolyte salt known in the art may be used to control ionic strength and/or pH of the final formulations. When used herein the buffer or electrolyte salt is preferably present at a concentration of from about 0.001 wt % to about 20 wt %, more preferably 0.05 wt % to about 1 wt %, even more preferably from about 0.05 wt % to about 0.5 wt %, and most preferably 0.1 wt % to about 0.5 wt %.

B. Oxidants

The compositions of the present invention can also, optionally, contain oxidants and/or bleaching agents. Preferred oxidants include, but are not limited to, hydrogen peroxide, alkaline metal salts and/or alkaline earth metal salts of hypochlorous acid, hypochlorous acid, solubilized chlorine, any source of free chlorine, solubilized chlorine dioxide, acidic sodium chlorite, active chlorine generating compounds, active oxygen generating compounds, chlorine-dioxide generating compounds, solubilized ozone, sodium potassium peroxysulfate, sodium perborate, and combinations thereof. The oxidant can be present at a level of from 0.001% to 10%, or from 0.01% to 10%, or from 0.1% to 5% by weight, or from 0.5% to 2.5% by weight.

C. Antimicrobial Agents

The compositions of the present invention can also, optionally, contain antimicrobial (germicidal) agents or biocidal agents. Such antimicrobial agents can include, but are not limited to, alcohols, chlorinated hydrocarbons, organometallics, halogen-releasing compounds, metallic salts, pine oil, organic sulfur compounds, iodine compounds, silver nitrate, quaternary ammonium compounds (quats), chlorhexidine salts, and/or phenolics. Antimicrobial agents suitable for use in the compositions of the present invention are described in U.S. Pat. Nos. 5,686,089; 5,681,802, 5,607,980, 4,714,563; 4,163,800; 3,835,057; and 3,152,181, each of which is herein incorporated by reference in its entirety. Also useful as antimicrobial agents are the so-called "natural" antibacterial actives, referred to as natural essential oils. These actives derive their names from their natural occurrence in plants. Suitable antimicrobial agents include alkyl alpha-hydroxyacids, aralkyl and aryl alpha-hydroxyacids, polyhydroxy alpha-hydroxyacids, polycarboxylic alpha-hydroxyacids, alpha-hydroxyacid related compounds, alpha-ketoacids and related compounds, and other related compounds including their lactone forms. Preferred antimicrobial agents include, but are not limited to, alcohols, chlorinated hydrocarbons, organometallics, halogen-releasing compounds, metallic salts, pine oil, organic sulfur compounds, iodine, compounds, antimicrobial metal cations and/or antimicrobial metal cation-releasing compounds, chitosan, quaternary alkyl ammonium biocides, phenolics, germicidal oxidants, germicidal essential oils, germicidal botanical extracts, alpha-hydroxycarboxylic acids, and combinations thereof. When incorporated herein the antimicrobial agent is preferably present at a concentration of from about 0.001 wt % to about 10 wt %, more preferably 0.05 wt % to about 1 wt %, even more preferably from about 0.05 wt % to about 0.5 wt %, and most preferably 0.1 wt % to about 0.5 wt %.

D. Solvents

Water may be used as a solvent alone, or in combination with any suitable organic solvents. Such solvents may include, but are not limited to, $C_{1-6}$ alkanols, $C_{1-6}$ diols, $C_{1-10}$ alkyl ethers of alkylene glycols, $C_{3-24}$ alkylene glycol ethers, polyalkylene glycols, short chain carboxylic acids, short chain esters, isoparafinic hydrocarbons, mineral spirits, alkylaromatics, terpenes, terpene derivatives, terpenoids, terpenoid derivatives, formaldehyde, and pyrrolidones. Alkanols include, but are not limited to, methanol, ethanol, n-propanol, isopropanol, butanol, pentanol, and hexanol, and isomers thereof. In one embodiment of the invention, water comprises at least 80% of the composition by weight, or at least 90% of the composition by weight or at least 95% of the composition by weight. In another embodiment of the invention, the organic solvents can be present at a level of from 0.001% to 10%, or from 0.01% to 10%, or from 0.1% to 5% by weight, or from 1% to 2.5% by weight.

E. Surfactants

The compositions of the present invention may contain surfactants selected from nonionic, anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. The surfactants may be present at a level of from about 0% to 90%, or from about 0.001% to 50%, or from about 0.01% to 25% by weight. Alternatively, surfactants may be present at a level of from about 0.1 to 10% by weight, or from about 0.1 to 5% by weight, or from about 0.1 to 1% by weight.

F. Additional Adjuvants

The compositions of the present invention may optionally contain one or more of the following adjuncts: stain and soil repellants, lubricants, odor control agents, perfumes, fragrances and fragrance release agents, and bleaching agents. Other adjuncts include, but are not limited to, acids, bases, dyes and/or colorants, solubilizing materials, stabilizers, thickeners, defoamers, hydrotropes, cloud point modifiers, preservatives, chelating agents, water-immiscible solvents, enzymes and other polymers.

The compositions of the present invention may be used by distributing, e.g., by placing the aqueous solution into a dispensing means, preferably a spray dispenser and spraying an effective amount onto the desired surface or article. An effective amount as defined herein means an amount sufficient to modify the surface of the article to achieve the desired benefit, for example, but not limited to soil repellency, cleaning and/ or disinfectancy. Distribution can be achieved by using a spray device, such as a trigger sprayer or aerosol, or by other means including, but not limited to a roller, a pad, a wipe or wiping implement, sponge, etc.

In another embodiment, a surface, an article or a device may be treated with the compositions of the present invention by immersing them or exposing the desired portion of the article or device to be treated to a bulk liquid solution containing the described PECs in the form of a treatment composition. Suitable immersion methods include baths, dipping tanks, wet padding and wet rolling application means common to the art. Such means are also suitable for forming premoistened wipes wherein a carrier substrate such as a woven material (cloth, towel, etc.) or a non-woven material (paper towel, tissue, toilet tissue, bandage) that may be dipped or padded with the described PEC compositions.

V. Measurement of Particle Sizes and Zeta Potentials

The diameters of the PECs (in nanometers) and their zeta potentials were measured with a Zetasizer ZS (Malvern Instruments). This instrument employs DLS, also known as Photon Correlation spectroscopy, to determine the diameters of colloidal particles in the range from about 0.1 nm to about 10000 nm.

The Zetasizer ZS instrument offers a range of default parameters which can be used in the calculation of particle diameters from the raw data (known as the correlation function or autocorrelation function). The diameters of the PECs reported herein were determined using a simple calculation model, in which the optical properties of the PECs were assumed to be similar to spherical particles of polystyrene latex particles, a common calibration standard used for more complex DLS experiments. In addition, the software package supplied with the Zetasizer provides automated analysis of the quality of the measurements made, in the form of "Expert Advice". The diameters described herein (specifically what is known as the "Z" average particle diameter) were calculated from raw data that met "Expert Advice" standards consistent with acceptable results, unless otherwise noted. In other words, the simplest set of default measurement conditions and calculation parameters were used to calculate the diameters of all of the PECs described herein, in order to facilitate direct comparison of PECs based on a variety of polymers, and avoiding the use of complex models of the scattering which could complicate or prevent comparisons of the diameters of PECs of differing chemical composition. Those skilled in the art will appreciate the particularly simple approach taken here, and realize that it is a valid approach to comparing and characterizing the PECs.

The Zetasizer ZS instrument instrument calculates the zeta potential of colloidal particles from measurements of the electrophoretic mobility, determined via a Doppler laser velocity measurement. The relationship between the electrophoretic mobility (a measurement of the velocity of a charged colloidal particle moving in an electric field) and the zeta potential (electric charge, expressed in units of millivolts) is well known. As in the particle size measurements, to facilitate direct comparison of PECs based on a variety of polymers, the simplest set of default measurement conditions were used. In other words, the aggregates were assumed to behave as polystyrene latex particles, and the Smoluchowski model relating the electrophoretic mobility and the zeta potential was used in all calculations. Unless otherwise noted, the mean zeta potentials described herein were calculated from raw data that met "Expert Advice" standards consistent with acceptable results. PECs bearing a net cationic (positive) charge will exhibit positive values of the zeta potential (in mV), while those bearing a net anionic (negative) charge will exhibit negative values of the zeta potential (in mV).

VI. Quartz Crystal Microgravimetry with Dissipation

Quartz Crystal Microgravimetry with Dissipation (QCM-D) offers an ideal experimental setup for fast, flow-cell or static measurements of adsorption at the solid-liquid interface. Applicants have used QCM-D to quantify adsorption of PECs produced via dilution of PECs precursor solutions at the solid-solution interface, where the solid is a silicon dioxide sensor surface (QSX 303 QCM-D sensors, obtained from Q-Sense.)

QCM-D measurements utilize a thin quartz disc sensor sandwiched between a pair of electrodes. When AC voltage is applied, the piezoelectric quartz crystal oscillates. The resonance frequency (f) of the crystal depends on the total oscillating mass, including water coupled to the oscillation. f decreases when a thin film is attached to the sensor crystal. This decrease is proportional to mass of film, if the film is thin and rigid. The mass (m) of the adhering layer can be calculated by using the Sauerbrey relation, $\Delta m = -\Delta fC/n$, where $C = 17.7$ ng Hz$^{-1}$ cm$^{-2}$ for a ~5 MHz quartz crystal and n=1, 3, 5, 7, 9, 11 is the overtone number (see Sauerbrey, G. Z. Phys. 1959, 15, 206-222). Soft, viscoelastic films do not fully couple to crystal oscillation, and for such films, the Sauerbrey relation underestimates mass on surface. Soft films dampen the oscillation of the crystal. This damping or dissipation (D) of the crystal's oscillation reveals the film's viscoelasticity. D is defined as $D = E_{dissipated}/(2\pi E_{stored})$, where $E_{dissipated}$ is dissipated or lost energy during one oscillation cycle, and $E_{stored}$ is the total amount of energy stored in the oscillator. Soft films, dissipating films, or films from viscoelastic fluids should be modeled, and should not be analyzed by the Sauerbrey relation.

Q-Sense, the manufacturer of the instrument used in our measurements, recommends use of the Sauerbrey relation if $\Delta D \leq 2 \times 10^{-6}$. Thus, the results described herein exclusively use the Sauerbrey relation, as the adsorbed layers delivered by PECs were not viscoelastic.

QCM-D was performed using a Q-Sense E4, which is designed to run four simultaneous experiments. In this work, four identical experiments were performed simultaneously. Prior to use, sensors were cleaned in plasma cleaner (Harrick PDC-32G) at medium RF, for 20 minutes. Clean, dry sensors were mounted in the four flow-through modules, and the experimental setup was equilibrated at 25.0±0.02° C. with ultrapure water or buffer flow at 150 µL/min until the frequency and dissipation baselines were level. Frequencies were monitored such that drift of 3rd harmonic was ≤1.5 Hz/hr. Each experiment began with flow-through of buffer at 150 µL/min for 10 minutes to establish a reference zero baseline. After 10 minutes, the pump was stopped briefly in order to switch from buffer to PEC solution. PEC solution was pumped through the modules until adsorption plateaued. Thereafter, the pump was stopped and the inflow solution was switched back to buffer for rinsing. After each quadrupled experiment, 50/50 ethanol/water was pumped over sensors to remove PECs from flow-through surfaces.

Data reproducibility was checked by four simultaneous experiments, using same solution container for all four inlet tubing inputs. The temperature of the measuring chamber was kept at 25.0° C.±0.02° C. with a Peltier unit. The average relative humidity was 45%, and the average lab temperature was 21° C. The data from overtone frequencies 3, 5, 7, 9, and 11 was averaged over all self-consistent sensor outputs.

VII. Examples

Example 1

PEC Precursor Solutions Comprising Poly(Diallyldimethyl Ammonium Chloride) (DADMAC) and Poly(Acrylic Acid) (PAA) and DLS Characterization of PECs Produced by Dilution Table 1.1 summarizes the compositions of several PEC precursor solutions in which the R value was varied from significantly less than 1, to 1.33 and to significantly greater than 1. In addition, the compositions were designed to have acidic pH levels, in order to be compatible with diluents comprising sources of hypochlorite ions such that the final aqueous solutions could, if desired, comprise hypochlorous acid.

The PEC precursor solutions comprising DADMAC and PAA were prepared in the following manner. An aqueous solution of DADMAC (40% polymer actives) was weighed and dispensed into a glass beaker followed by the appropriate volume of water required to achieve the desired total polymer concentration. This solution was thoroughly mixed using simple agitation. Finally, an aqueous solution of PAA (26% polymer actives) was weighed and added to the solution followed by mixing by simple agitation. The resulting precursor solutions were viscous, clear to clear-blue liquids without insoluble macroscopic particles. The total polymer concentration is defined by summing the moles of the repeat units of DADMAC and PAA polymers present in the precursor solutions. That is, Concentration=wt % DADMAC/MW$_{DADMAC}$+wt % PAA/MW$_{PAA}$ where MWD$_{ADMAC}$ and MW$_{PAA}$ are the molecular weight of the repeat units of DADMAC and PAA, respectively.

The diluted solutions comprising PECs can be prepared by diluting the PEC precursor solutions in any convenient manner. In this example, the precursor solutions were dispensed into a beaker, followed by addition of a volume of water or aqueous diluent to produce the diluted compositions comprising PECs. Alternatively, the order can be reversed wherein the precursor solution can be directly added to an appropriate volume of water or an aqueous diluent. In this example the solution was mixed via a magnetic stirbar for about 5 minutes to produce the diluted solutions comprising PECs. The diluted solutions were free of precipitates, free of flocculant, and suitable for analysis via dynamic light scattering, as described.

As described herein, the R value of the PEC precursor solutions may be adjusted to control the R value of the final PECs produced upon dilution. By controlling the R value of the PECs, the composition of the PECs, and hence the net charge (as measured by the mean zeta potential) on the PECs produced by dilution may be controlled. This control of the compositions and zeta potential of the PECs produced by dilution is achieved because the PEC precursor solutions comprise the polyelectrolytes in completely soluble form, free of coacervate or precipitates, which may be achieved via the methods taught herein.

diluted in steps, from 2000 mM to 250 mM to 50 mM to 1.5 mM. Formulation DADPAA 5 was also diluted in steps, from 2000 mM to 250 mM to 1.5 mM. Formulations DAD PAA 6-8 were diluted directly from 2000 mM to 1.5 mM.

The results in Table 1.3 also show the surprising result that stable PECs, even with compositions described by R values less than 1.0, may exhibit positive (cationic) values of the mean zeta potential. This is achieved in this example by ensuring the pH of the diluted aqueous solutions comprising the PECs was sufficiently acidic (about pH 3.6) to cause a significant fraction of the carboxylic acid groups of the

TABLE 1.1

PEC Precursor Compositions

| Formulation Name | DADMAC, grams | PAA, grams | Water, grams | DADMAC, wt % | PAA, wt % | Total polymer concentration, mM | pH | R value | Precipitate |
|---|---|---|---|---|---|---|---|---|---|
| DADPAA 1 | 13.53 | 18.14 | 18.33 | 10.7 | 9.5 | 2000 | 2.13 | 0.5 | No |
| DADPAA 2 | 32.48 | 5.44 | 12.08 | 25.8 | 2.8 | 2000 | 2.67 | 4.0 | No |
| DADPAA 3 | 4.92 | 11.68 | 33.40 | 18.4 | 6.1 | 2000 | 2.33 | 1.33 | No |

Notes:
DADMAC (Floquat 4540, SNF Inc., aqueous solution with 40% polymer actives), PAA (Aquatreat AR4, Akzo Nobel, aqueous solution with 26% polymer actives)

TABLE 1.2

PEC Compositions Produced Via Dilution of PEC Precursors from Table 1.1

| Formulation Name | Precursor Composition | Precursor, grams | Water, grams | DADMAC, mM | PAA, mM | Total polymer concentration, mM | pH |
|---|---|---|---|---|---|---|---|
| DADPAA 4 | DADPAA 1 | 0.38 | 499.63 | 0.5 | 1.0 | 1.5 | 3.62 |
| DADPAA 5 | DADPAA 1 | 0.38 | 499.63 | 0.5 | 1.0 | 1.5 | 3.57 |
| DADPAA 6 | DADPAA 1 | 0.38 | 499.63 | 0.5 | 1.0 | 1.5 | 3.59 |
| DADPAA 7 | DADPAA 2 | 0.38 | 499.63 | 1.2 | 0.3 | 1.5 | 4.01 |
| DADPAA 8 | DADPAA 3 | 0.38 | 499.63 | 0.86 | 0.64 | 1.5 | 3.70 |

TABLE 1.3

Z-average diameters and zeta potentials of PECs Produced Via Dilution of Precursor Compositions from Table 1.1

| Formulation Name | R value | Total Polymer concentration, mM | Z-average diameter, nm | Zeta Potential, mV | Comments |
|---|---|---|---|---|---|
| DADPAA 4 | 0.5 | 1.5 | 92.80 (n = 3) | +41.7 | Step diluted, water added to precursor |
| DADPAA 5 | 0.5 | 1.5 | 93.28 (n = 3) | +37.2 | Step diluted, water added to precursor |
| DADPAA 7 | 4.0 | 1.5 | 173.4 (n = 3) | +39.4 | water added to precursor |
| DADPAA 8 | 1.33 | 1.5 | 180.0 (n = 3) | +57.0 | water added to precursor |

The results in Table 1.3 indicate that PECs with average diameters that will result in colloidal stability (less than 500 nm, more preferably less than 250 nm, even more preferably less than 100 nm can be formed upon dilution of PECs precursor solutions. Aqueous solutions comprising PECs at very low total polymer concentrations, in this example at only 1.5 mM, are very effective in the modification of a wide variety of surfaces, both inanimate (glass, tile, fabrics) and animate (bacterial spores, virus particles), due to the rapid adsorption of PECs onto such surfaces. The PEC precursor solutions of this example thus show how very convenient formulations that provide aqueous PECs upon very large dilution factors (2000 mM to 1.5 mM total polymer dilution, or 1333.3 times dilution) may be achieved. Formulation DADPAA 4 was anionic polymer (here PAA) to exist in their protonated (non-ionized) form, resulting in the net zeta potential of the PECs to be determined by the presence of the cationic groups of the DADMAC polymer chains incorporated in the PECs.

The inventors speculate, without being bound by theory, that the use of PEC precursor solutions comprising fully soluble polyelectrolytes, which may be achieved as taught herein, allows the controlled and rapid formation of PECs during the dilution process because the polyelectrolytes are initially fully soluble, relatively flexible, and thus able to easily relax into conformations favoring electrostatic interactions between the charged groups on the polyelectrolytes of opposite charge, forming PECs of appropriately small size upon simple dilution, without the requirement for large amounts of mechanical energy input. In other words, the PECs are assembled rapidly during the dilution process, and then are separated from one another upon further dilution, as opposed to the formation of insoluble macroscopic particles comprising the oppositely charged polyelectrolytes, which then must be processed to reduce the average particle size through extremely high shear mixing or additional steps comprising recovery of the insoluble PEC particles.

Example 2

Compositions of PEC Precursor Solutions and DLS Characterization of PECs Produced by Dilution Comprising Chitosan (a Natural Polymer) and Poly(Acrylic Acid) (PAA)

Details of exemplary PEC precursor solutions comprising a natural polymer (chitosan) and PAA at R values both less than and significantly greater than 1.0 are summarized in Table 2.1. In order to ensure the solubility of chitosan in the precursor solutions, the pH was adjusted to be acidic, which causes the formation of cationic charges on the amine groups of the chitosan. Since PAA is soluble in aqueous solutions in its protonated acid form, the PECs precursor solutions were clear and free of coacervates or precipitates.

Precursor solutions of chitosan and PAA can be prepared in a manner similar to PAA and DADMAC solutions. Chitosan, when sourced as a solid powder, may first be dissolved into an acidic aqueous stock solution (e.g., hydrochloric acid or citric acid). In this example, the chitosan stock was then diluted with water, and the pH adjusted to less than 3.0, followed by addition of the aqueous solution of PAA. Mixing with simple agitation completed the preparation. Precipitation of the precursor solutions can be avoided by maintaining an acidic pH. In this example, no precipitates were observed if the pH of the precursor solution was below 3.5.

Diluted solutions comprising PECs can be prepared by adding a volume of the precursor solutions into an appropriate volume of water required to reach the final total polymer concentration desired. Continuous agitation or mixing during the dilution aids in the formation of colloidal stable PECs. Once the solution has been thoroughly mixed, the pH can be adjusted by adding acid or base depending on the desired pH value. Precipitation within the diluted solutions comprising PECs can be avoided by maintaining an acidic pH. In this example, in which chitosan is the polyelectrolyte capable of developing a cationic charge at acidic pH values, no precipitates were observed where the pH was below 3.5.

TABLE 2.1

PEC Precursor Compositions Comprising Chitosan and PAA

| Formulation Name | Chitosan grams | PAA, grams | HCl, grams | Water, grams | Chitosan, wt % | PAA, wt % | Total polymer concentration, mM | pH | R value | Precipitate |
|---|---|---|---|---|---|---|---|---|---|---|
| CPAA 1 | 4.27 | 0.91 | 1.00 | 13.82 | 1.3 | 1.2 | 250 | 3.46 | 0.5 | No |
| CPAA 2 | 10.26 | 0.27 | 1.00 | 8.47 | 3.2 | 0.44 | 250 | 3.44 | 4.0 | No |
| CPAA 3 | 15.81 | 3.36 | 1.00 | — | 4.9 | 4.4 | 925 | 3.27 | 0.5 | No |
| CPAA 4 | 18.67 | 0.50 | 1.00 | — | 5.8 | 0.65 | 455 | 3.20 | 4.0 | No |

Notes:
Chitosan, (Hydagen HCMF, Cognis, 6% acidic solution: 2.0 grams chitosan, 10.0 grams 1.0M HCl, 20.0 grams water), PAA (Aquatreat AR4, Akzo Nobel, aqueous solution with 26% polymer actives)

TABLE 2.2

PEC Compositions Produced Via Dilution of Precursor Compositions from Table 2.1

| Formulation Name | Precursor Composition | Precursor, grams | HCl, grams | Water, grams | Chitosan, mM | PAA, mM | Total polymer concentration, mM | R value | pH | Precipitate |
|---|---|---|---|---|---|---|---|---|---|---|
| CPAA 5 | CPAA 1 | 1.20 | 1.00 | 197.80 | 0.5 | 1.0 | 1.5 | 0.5 | 3.5 | No |
| CPAA 6 | CPAA 2 | 1.20 | 1.00 | 197.80 | 1.2 | 0.3 | 1.5 | 4.0 | 3.4 | No |
| CPAA 7 | CPAA 3 | 1.32 | 1.34 | 198.34 | 0.5 | 1.0 | 1.5 | 0.5 | 3.3 | No |
| CPAA 8 | CPAA 4 | 1.66 | 1.34 | 198.00 | 1.2 | 0.3 | 1.5 | 4.0 | 3.2 | No |
| CPAA 9 | CPAA 3 | 0.32 | — | 199.68 | 0.5 | 1.0 | 1.5 | 0.5 | 4.0 | Yes |
| CPAA 10 | CPAA 4 | 0.66 | — | 199.34 | 1.2 | 0.3 | 1.5 | 4.0 | 4.0 | Yes |

TABLE 2.3

Z-average diameters and zeta potentials of PECs Produced Via Dilution of Precursor Compositions from Table 2.1

| Formulation Name | R value | Total Polymer concentration, mM | Z-average diameter, nm | Zeta Potential, mV | Comments |
|---|---|---|---|---|---|
| CPAA 5 | 0.5 | 1.5 | 177.3 (n = 3) | +34.5 | Precursor added into water |
| CPAA 6 | 4.0 | 1.5 | 295.7 (n = 3) | +52.3 | Precursor added into water |
| CPAA 7 | 0.5 | 1.5 | 545.5 (n = 3) | +39.7 | Precursor added into water |
| CPAA 8 | 4.0 | 1.5 | 214.0 (n = 3) | +53.5 | Precursor added into water |

The results in Table 2.3 indicate that PEC precursor solutions comprising chitosan, a polymer comprising amine groups capable of developing a cationic charge at acidic pH values, and PAA, a polymer comprising carboxylic acid groups, yield stable PECs when diluted. As in Example 1, the PECs formed from precursor solutions with R values of less than 1.0 exhibit a cationic charge due to the presence of cationic charges on the chitosan polymer chains and the presence of the acid form of the anionic groups on the PAA chains when the desired pH of the diluted PECs solution is controlled to be acidic.

The results in Table 2.3 also illustrate one way to adjust the size of the PECs formed by dilution of a precursor solution. Although formulation CPAA 3 is a clear solution free of coacervates and precipitates, the Z-average diameter of the PECs formed from dilution was larger (545.5 nm) than may be preferred for optimum colloidal stability. Reduction of the total polymer concentration in the precursor solution at the same R value (Formulation CPAA 1) yields smaller PECs of similar zeta potential upon dilution to the same desired polymer concentration. Thus, the total polymer concentration of the precursor solution may be adjusted, without other changes, in order to control the size of the PECs formed upon dilution, which in turn determines the relative colloidal stability of the PECs formed via dilution.

The results in Table 2.3 also indicate that the formation of PECs via dilution of precursor solutions does not depend on the details of the manner of dilution. In other words, the dilution of the precursors in Example 2 was made by dropping an appropriate volume of the precursor solution into water under simple agitation provided by a magnetic stirrer. This is in contrast to how dilution was achieved in Example 1, where a small volume of the precursor solution was placed in a beaker, followed by a stirbar to provide moderate agitation, and then an appropriate volume of water was quickly added.

Example 3

PEC Precursor Solutions Comprising Lupasol and Poly(Acrylic Acid) (PAA) and DLS Characterization of PECs Produced by Dilution Precursor solutions of Lupasol (a synthetic polymer) and PAA can be prepared in a manner similar to PAA and DAD-MAC solutions. The appropriate amount of Lupasol was first diluted into an acidic solution of sodium chloride and then combined with an appropriate amount of an aqueous solution of PAA. Mixing with simple agitation completed the preparation. Diluted solutions comprising PECs were prepared by adding a volume of the precursor solutions into an appropriate volume of water required to reach the ultimate total polymer concentration desired. Simple mixing during the dilution was achieved via a magnetic stirbar. Once the solution has been thoroughly mixed, the pH can be adjusted by adding acid or base depending on the desired pH value. Precipitation of the precursor solutions can be avoided by maintaining an acidic pH. In this example, no precipitates were observed if the pH of the precursor solution was below 3.5. Precipitation of the precursor solutions can also be avoided by the addition of excess electrolyte. In this example, no precipitates were observed if 500 mM sodium chloride was present in the precursor solution.

As shown in Table 3.1, a PEC precursor solution designed to yield PECs in an acidic solution comprising Lupasol (which develops a cationic charge at acidic pH values) and PAA can be produced through the addition of an electrolyte (NaCl) to the precursor solution.

TABLE 3.1

PECs Precursor Compositions

| Formulation Name | Lupasol grams | PAA, grams | NaCl, grams | HCl, grams | Water, grams | Lupasol, wt % | PAA, wt % | Total polymer concentration, mM | NaCl, mM | pH | R value | Precipitate |
|---|---|---|---|---|---|---|---|---|---|---|---|---|
| LupPAA 1 | 1.44 | 9.07 | 2.00 | 3.00 | 4.49 | 1.33% | 1.18% | 250 | 500 | 2.34 | 0.5 | No |
| LupPAA 2 | 3.45 | 2.72 | 2.00 | 3.00 | 8.83 | 3.18% | 0.36% | 250 | 500 | 2.51 | 4.0 | No |
| LupPAA 3 | 1.44 | 9.07 | 2.00 | — | 7.49 | 1.33% | 1.18% | 250 | 500 | 3.84 | 0.5 | Yes |
| LupPAA 4 | 3.45 | 2.72 | 2.00 | — | 11.83 | 3.18% | 0.36% | 230 | 500 | 9.83 | 4.0 | Yes |
| LupPAA 5 | 1.44 | 9.07 | — | 3.00 | 9.49 | 1.33% | 1.18% | 250 | 0 | 2.25 | 0.5 | Yes |
| LupPAA 6 | 3.45 | 2.72 | — | 3.00 | 13.83 | 3.18% | 0.36% | 250 | 0 | 2.52 | 4.0 | No |

Notes:
Lupasol (Lupasol P, BASF, aqueous solution used at 5% polymer actives), PAA (Aquatreat AR4, Akzo Nobel, aqueous solution with 2.6% polymer actives), NaCl (5.0M aqueous solution), HCl (1.0M aqueous solution)

TABLE 3.2

PEC Compositions Produced Via Dilation of Precursor Compositions from Table 3.1

| Formulation Name | Precursor Composition | Precursor, grams | Water, grams | Lupasol, mM | PAA, mM | Total polymer concentration, mM | R value | pH | Precipitate |
|---|---|---|---|---|---|---|---|---|---|
| LupPAA 7 | LupPAA 1 | 0.60 | 99.40 | 0.5 | 1.0 | 1.5 | 0.5 | 3.39 | No |
| LupPAA 8 | LupPAA 2 | 0.60 | 99.40 | 1.2 | 0.3 | 1.5 | 4.0 | 3.49 | No |

TABLE 3.3

Z-average diameter and zeta potential of PECs Produced
Via Dilution of Precursor Compositions from Table 3.1

| Formulation Name | R value | Total Polymer concentration, mM | Z-average diameter, nm | Zeta Potential, mV | Comments |
|---|---|---|---|---|---|
| LupPAA 6* | 4.0 | 1.5 | 57.13 | +43.9 | Precursor added into water |

The results in Table 3.3 show that a PEC precursor solution comprising a polymer capable of developing a cationic charge (the branched polyethyleneimine polymer Lupasol P) and a polymer capable of developing an anionic charge (PAA) yields a stable PEC upon dilution. Since the R value is greater than 1.0, the PECs formed upon dilution exhibit a cationic (positive) zeta potential, as expected.

Example 4

Compositions of PECs Precursor Solution and DLS Characterization of PECs Produced by Dilution Comprising DADMAC and Poly(Vinyl Sulfate)

Precursor solutions of DADMAC and poly(vinyl sulfate) (PVS), a polyelectrolyte with anionic charged groups (sulfate groups), can be prepared in a manner similar to PAA and DADMAC solutions. An aqueous solution of DADMAC was first diluted in the appropriate of amount water followed by the addition of the appropriate amount of an aqueous solution of poly(vinyl sulfate). Mixing with simple agitation completed the preparation. Diluted solutions comprising PECs can be prepared by adding a volume of the precursor solutions, with simple stirring, into the appropriate volume of water required to reach the ultimate total polymer concentration desired. Optionally, an electrolyte or oxidant can be added (e.g., added to the water used for the dilution step). Once the solution has been thoroughly mixed, the pH can be adjusted by adding acid or base depending on the desired pH value.

Sodium chloride was used as a substitute for sodium hypochlorite in the formulations of Example 4, in order to ensure measurement of the zeta potential of the PECs produced via dilution was not compromised by the presence of the oxidant.

The PEC precursor compositions summarized in Table 4.1 show that clear, stable precursor solutions may comprise DADMAC, a polyelectrolyte with cationic charges due to quaternary ammonium groups, which do not exhibit a dependence on the pH of the aqueous precursor solution. These precursor compositions also comprise poly(vinyl sulfate), a polyelectrolyte with sulfate groups, which are also not particularly sensitive to the pH of the aqueous solutions, i.e., the pKa of the sulfate groups is estimated to be significantly less than 4, and less than about 2.

PEC precursor solutions comprising DADMAC and PVS, with R values greater than 1.0, are especially suitable for dilution with aqueous solutions comprising sodium hypochlorite, to provide PECs in the diluted aqueous solutions in combination with the hypochlorite ion and hypochlorous acid, which can provide rapid stain removal and antimicrobial properties useful in cleaning healthcare facilities or as additives in laundering processes done by consumers.

TABLE 4.1

PECs Precursor Compositions

| Formulation Name | DADMAC, grams | PVS, grams | Water, grams | DADMAC, wt % | PVS, wt % | Total polymer concentration, mM | R value | Precipitate |
|---|---|---|---|---|---|---|---|---|
| DADPVS 1 | 1.35 | 3.47 | 0.18 | 10.7 | 17.4 | 2000 | 0.5 | No |
| DADPVS 2 | 3.25 | 1.04 | 0.71 | 25.8 | 5.2 | 2000 | 4.0 | No |

Notes:
DADMAC (Floquat 4540, SNF Inc., aqueous solution with 40% polymer actives), Poly(vinyl sulfate), (Sigma Aldrich, sodium salt, aqueous solution with 25% polymer actives)

TABLE 4.2

Compositions of PECs Produced Via Dilution of Precursor Compositions from Table 4.1

| Formulation Name | Precursor Composition | Precursor grams | NaCl, grams | Water, grams | DADMAC mM | PVS mM | Total polymer concentration, mM | R value | pH | NaCl mM | Precipitate |
|---|---|---|---|---|---|---|---|---|---|---|---|
| DADPVS 3 | DADPVS 1 | 0.13 | 2.00 | 97.88 | 0.83 | 1.67 | 2.5 | 0.5 | 2.0 | 100 | Yes |
| DADPVS 4 | DADPVS 1 | 0.30 | 2.00 | 97.70 | 2.00 | 4.00 | 6.0 | 0.5 | 5.5 | 100 | Yes |
| DADPVS 5 | DADPVS 2 | 0.75 | 2.00 | 97.25 | 12.0 | 3.00 | 15.0 | 4.0 | 6.75 | 100 | No |
| DADPVS 6 | DADPVS 2 | 0.75 | — | 99.25 | 12.0 | 3.00 | 15.0 | 4.0 | 6.80 | 0 | No |

Although Formulations DADPVS 3 and DADPVS 4 showed the presence of precipitate at an R value of 0.5, it is believed that the addition of additional NaCL or hypochlorite salt (e.g., NaOCl) electrolyte (e.g., 500 mM) would be sufficient to prevent precipitate formation.

TABLE 4.3

Z-average diameter and zeta potential of PECs Produced
Via Dilution of Precursor Compositions from Table 4.2

| Formulation Name | R Value | Total Polymer concentration, mM | Z-average diameter, nm | Zeta Potential, mV | Comments |
|---|---|---|---|---|---|
| DADPVS 5 | 4.0 | 15 | 66.33 | +28.4 | Diluted with water containing 100 mM NaCl as electrolyte |
| DADPVS 6 | 4.0 | 15 | 61.64 | +29.3 | Diluted with deionized water, precursor to water |

The results in Table 4.3 show that stable PECs, at total polymer concentrations of 15 mM (significantly higher than in examples 1-3) are produced via dilution of the precursor solution with deionized water. The PECs produced exhibit a cationic (positive) zeta potential, as expected, since R is significantly greater than 1.0.

The results in Table 4.3 also show that stable PECs may be produced via dilution of the precursor solutions with an aqueous diluent comprising significant amounts of an electrolyte. Sodium chloride was used as a substitute for sodium hypochlorite in Example 4, in order to ensure measurement of the zeta potential of the PECs produced via dilution was not compromised by the presence of the oxidant. It is believed, without being bound by theory, that the difference between the chloride and hypochlorite salts is immaterial to stability, both being electrolytes, in terms of their effects on the initial formation of the PECs via the dilution process. The results also show that the diameters of the PECs produced via dilution in deionized water or water with electrolyte are similar, i.e, the rapid assembly of PECs during the dilution process, even with the presence of additional electrolytes, is readily achieved and does not require significant changes in the dilution process to accommodate electrolytes or oxidants like hypochlorite in the dilution liquid employed.

Example 5

Characterization of PECs Produced Via Dilution of PEC Precursor Solutions and Direct Assembly of PECs Under Dilute Conditions Aqueous solutions comprising PECs produced via dilution from PEC precursor solutions were compared with aqueous solutions comprising PECs made via the direct assembly method taught in US 201110236582. Some of the compositions also included NaCl as an electrolyte, and as a substitute for sodium hypochlorite, for reasons described in Example 4.

The precursor solutions comprising DADMAC and PAA were prepared using a procedure identical to the procedure described in Example 1. An aqueous solution of DADMAC was weighed and dispensed into a glass beaker followed by the appropriate volume of an aqueous solution of succinic acid (5 wt %) and additional water. This solution was thoroughly mixed using simple agitation. Finally, an aqueous solution of PAA (26% polymer actives) was weighed and added to the solution followed by mixing by simple agitation. The resulting precursor solutions were viscous, clear to clear-blue liquids without insoluble macroscopic particles. The ultimate solutions of diluted PECs were prepared by dispensing the precursor solution into an appropriate vessel, followed by introduction of a volume of water required to reach an ultimate total polymer concentration of approximately 1.6 mM. Once the solution was thoroughly mixed by simple agitation, the pH was adjusted to the desired pH value.

TABLE 5.1A

PECs Precursor Compositions used to prepare PECs via Dilution

| Formulation Name | DADMAC, grams | PAA, grams | Succinic Acid, grams | Water, grams | DADMAC, wt % | PAA, wt % | Total polymer concentration, mM | Succinic Acid, wt % | R value | Precipitate |
|---|---|---|---|---|---|---|---|---|---|---|
| DADPAA 9 | 5.20 | 7.00 | 61.47 | 26.40 | 2.06 | 1.83 | 385 | 3.07 | 0.5 | No |
| DADPAA 10 | 12.52 | 2.11 | 61.42 | 23.99 | 4.96 | 0.55 | 385 | 3.07 | 4.0 | No |

Notes:
DADMAC (Floquat 4540, SNF Inc., aqueous solution with 40% polymer actives), PAA (Aquatreat AR4, Akzo Nobel, aqueous solution with 26% polymer actives), Succinic Acid (5 wt % aqueous solution)

TABLE 5.1B

Compositions of PECs prepared via Dilution

| Formulation Name | Precursor sample | Precursor, grams | NaCl, grams | Water, grams | Total polymer concentration, mM | DADMAC, mM | PAA, mM | NaCl, mM | pH |
|---|---|---|---|---|---|---|---|---|---|
| DADPAA 11 | DADPAA 9 | 0.41 | 0 | 99.6 | 1.6 | 1.05 | 0.52 | 0 | 7.04 |
| DADPAA 12 | DADPAA 9 | 0.41 | 1.62 | 98.1 | 1.6 | 1.05 | 0.52 | 1.38 | 6.99 |
| DADPAA 13 | DADPAA 10 | 0.47 | 0 | 99.6 | 1.8 | 1.45 | 0.36 | 0 | 7.03 |
| DADPAA 14 | DADPAA 10 | 0.45 | 1.62 | 98.3 | 1.7 | 1.38 | 0.35 | 1.32 | 7.01 |

Notes:
NaCl (0.5 wt % aqueous solution)

Dilute PECs described by Tables 5.2A and 5.2B were prepared via the direct assembly method using the following procedure. Stock C (succinic acid solution), Stock D (sodium chloride solution), and water were first combined. Second, the minor polymeric component was added to the solution followed by the addition of the major polymeric component. After the solution was mixed by simple agitation, the pH was adjusted to the desired pH value.

TABLE 5.2A

Stock solutions Used for Direct Assembly of Dilute PECs

| Formulation Name | R Value | PAA Stock, grams | DADMAC Stock, grams | Stock C, grams | Stock D, grams | Water, grams |
|---|---|---|---|---|---|---|
| DADPAA 15 | 0.5 | 10.0 | 5.0 | 2.4 | 0 | 82.6 |
| DADPAA 16 | 0.5 | 10.0 | 5.0 | 2.4 | 1.6 | 81.1 |
| DADPAA 17 | 4.0 | 3.0 | 12.0 | 2.4 | 0 | 82.6 |
| DADPAA 18 | 4.0 | 3.0 | 12.0 | 2.4 | 1.6 | 81.1 |

Notes:
PAA Stock: Aquatreat AR4, Akzo Nobel, aqueous solution with 0.071% polymer actives.
DADMAC Stock: Floquat 4540, SNF Inc., aqueous solution with 0.161% polymer actives.
Stock C: Succinic Acid; 0.50 wt % aqueous solution.
Stock D: Sodium Chloride; 0.50 wt % aqueous solution

TABLE 5.2B

Final Compositions of Solutions with Direct Assembly of PECs

| Formulation Name | DADMAC, mM | PAA, mM | Total polymer concentration, mM | Succinic Acid, mM | NaCl, mM | pH | R value |
|---|---|---|---|---|---|---|---|
| DADPAA 15 | 0.50 | 1.00 | 1.5 | 1.0 | 0 | 6.99 | 0.5 |
| DADPAA 16 | 0.50 | 1.00 | 1.5 | 1.0 | 1.3 | 7.07 | 0.5 |
| DADPAA 17 | 1.20 | 0.30 | 1.5 | 1.0 | 0 | 7.03 | 4.0 |
| DADPAA 18 | 1.20 | 0.30 | 1.5 | 1.0 | 1.3 | 7.01 | 4.0 |

TABLE 5.3

Z average diameters and Zeta Potential of PECs Produced Via Dilution from Precursor Solutions or from a Direct Assembly Method

| Formulation Name | R Value | Total Polymer concentration, mM | Z-average diameter, nm | Zeta Potential, mV | Comments |
|---|---|---|---|---|---|
| DADPAA 11 | 0.5 | 1.5 | 392.9 | −54.2 | No NaCl |
| DADPAA 12 | 0.5 | 1.5 | 104.7 | −47.2 | NaCl |
| DADPAA 13 | 4.0 | 1.5 | 200.6 | +29.4 | No NaCl |
| DADPAA 14 | 4.0 | 1.5 | 184.2 | +31.5 | NaCl |
| DADPAA 15 | 0.5 | 1.5 | 244.4 | −51.5 | No NaCl |
| DADPAA 16 | 0.5 | 1.5 | 245.8 | −52.0 | NaCl |
| DADPAA 17 | 4.0 | 1.5 | 369.7 | +32.4 | No NaCl |
| DADPAA 18 | 4.0 | 1.5 | 371.5 | +34.9 | NaCl |

Notes -
Z-average diameters are means of triplicate analyses. Zeta potentials are means of duplicate analyses.

The results in Table 5.3 show that stable PECs may be produced via dilution of PEC precursor solutions at R values both below and above R=1.0. Since the pH of the diluted aqueous solutions was adjusted to be near neutral, (near pH 7), the PECs produced via the dilution method with R values less than 1.0 (DADPAA 5 and 6) exhibit anionic (negative) zeta potential values due to the excess of anionic groups provided by the ionized carboxylate groups of the PAA comprising the PECs. Alternatively, PECs with cationic (positive) zeta potential values may be produced via dilution of the PECs precursor solutions formulated at R values greater than 1.0 (DADPAA 7 and 8). All PECs produced via the dilution of precursor solutions exhibit Z-average diameters that are small enough (less than 500 nm) to ensure colloidal stability. The PECs were produced via dilution in either the absence or presence of electrolyte, indicating, as discussed elsewhere, that the assembly of PECs occurs rapidly during the dilution, and does not require any special changes in the dilution process when electrolyte (or an oxidant such as hypochlorite, which will behave similarly) is present.

The results in Table 5.3 also show that stable PECs produced via the direct assembly method also exhibit Z-average diameters small enough to ensure colloidal stability, and also zeta potential values which can be controlled via the R parameter.

The results in Table 5.3 also show that the mean zeta potential values of the PECs produced via the method of the instant invention, at a given R value with the same electrolyte concentration, are very similar to the zeta potential values of the PECs made via the direct assembly method. According to the manufacturer of the instrument used to determine the zeta potentials cited herein, the expected variation in zeta potential of a given sample should be about 10% relative.

The inventors believe, based on the trends in the results in Table 5.3, that the PECs produced via the dilution method of the instant invention are qualitatively similar to those produced via the direct assembly method. Thus, the present invention provides an important, new versatile approach to the use, production, and delivery of PECs of controlled size and charge.

Example 6

Compositions and Characterization of PECs Prepared Via Dilution of Precursor Solutions with Aqueous Solutions of Surfactants Aqueous solutions of PECs that also comprise surfactants of various types may be prepared via dilution of PECs precursor solutions with aqueous solutions of surfactants to deliver aqueous cleaning solutions suitable for hard surface cleaning. PEC precursor solutions may comprise one part, and a suitable aqueous solution of a surfactant may comprise a second part of a two part system in which the two parts are combined via a device that draws liquid from each of the separate parts into a stream of flowing water, producing a ready to use diluted aqueous formulation comprising PECs and surfactants. Such ready to use solutions may be useful in janitorial cleaning of floors and other hard surfaces, or could be directed to other parts of a liquid control system for the manipulation of the charge of bacterial or fungal spores or virus particles, or in the production of treated articles, including moving webs of nonwovens, paper, fibers, etc. PEC precursor solutions may also be diluted with aqueous solutions comprising surfactants and optionally, adjuvants such as buffers, via a package comprising a trigger sprayer capable of drawing liquids from two separate chambers of a dual-chamber bottle, to deliver a diluted solution in a ready to use, portable format.

The presence of surfactants in the final diluted solutions comprising PECs may be desirable in order to further reduce the surface tension (air-water tension) of the aqueous solutions to facilitate wetting or cleaning rates, while also providing PECs of controlled size and charge for the modification of substrate surfaces via the adsorption of PECs.

The compositions of PECs prepared by dilution with aqueous solutions comprising surfactants were prepared by one of two methods. Either the PECs precursors were diluted into water or buffer solution to form dilute PECs first, followed by the addition of surfactant at the desired concentration (e.g. DPQ 1 in Table 6.1), or PECs precursors were diluted into a solution containing the surfactant (e.g. DPQ2, DPSLS1, DPAO1, DPAO2 in Table 6.1).

TABLE 6.1

PEC Solutions Prepared by Dilution with Aqueous Solutions Comprising Surfactants

| Formulation Name | Precursor sample | Precursor, grams | Water, grams | Total polymer concentration, mM | R value | Succinic Acid, mM | Surfactant 1, grams | Surfactant 1, wt % | Surfactant 2, grams | Surfactant 2, wt % | Surfactant 3, grams | Surfactant 3, wt % | pH of final solution |
|---|---|---|---|---|---|---|---|---|---|---|---|---|---|
| DPQ 1 | DADPAA 10 | 0.19 | 49.8 | 1.5 | 4.0 | 1 0 | 0.18 | 0.02 | — | — | — | — | 7.04 |
| DPQ 2 | DADPAA 10 | 0.19 | 49.6 | 1.5 | 4.0 | 1.0 | 0.20 | 0.02 | — | — | — | — | 6.55 |
| DPSLS1 | DADPAA 9 | 0.19 | 49.8 | 1.5 | 0.5 | 1.0 | — | — | 0.18 | 0.02 | — | — | 6.42 |
| DPAO1 | DADPAA 9 | 0.19 | 49.6 | 1.5 | 0.5 | 1.0 | — | — | — | — | 0.20 | 0.02 | 6.88 |
| DPAO2 | DADPAA 10 | 0.19 | 49.6 | 1.5 | 4.0 | 1.0 | — | — | — | — | 0.20 | 0.02 | 6.63 |
| DADPAA 19 | DADPAA 9 | 0.19 | 49.8 | 1.5 | 0.5 | 1.0 | — | — | — | — | — | — | 6.94 |
| DADPAA 20 | DADPAA 10 | 0.19 | 49.8 | 1.5 | 4.0 | 1.0 | — | — | — | — | — | — | 7.10 |

Notes:
Surfactant 1: Quaternary ammonium surfactant; BTC 1010, Stepan Corp.; 5.0 wt % aqueous solution.
Surfactant 2: Sodium lauryl sulfate surfactant; SLS Crude, Stepan Corp.; 5.0 wt % aqueous solution.
Surfactant 3: Amine oxide surfactant; Ammonyx LO, Stepan Corp.; 5.0 wt % aqueous solution

TABLE 6.2

Characterization of PEC Solutions Prepared by Dilution with Aqueous Solutions Comprising Surfactants

| Formulation Name | R Value | Total Polymer concentration, mM | Z-average diameter, nm | Zeta Potential, mV | Comments |
|---|---|---|---|---|---|
| DPQ 1 | 4 | 1.5 | 159.4 | +32.2 | Quat into PECs |
| DPQ 2 | 4 | 1.5 | 170.6 | +32.4 | PECs into quat |
| DPSLS 1 | 0.5 | 1.5 | 164.5 | −62.7 | PECs into SLS |
| DPAO 1 | 0.5 | 1.5 | 135.1 | −52.6 | PECs into LO |
| DPAO 2 | 4.0 | 1.5 | 197.4 | +28.1 | PECs into LO |
| DADPAA 19 | 0.3 | 1.5 | 363.0 | −52.7 | No surf control |
| DADPAA 20 | 4.0 | 1.5 | 160.1 | +25.3 | No surf control |

The results in Table 6.2 show that PECs with Z-average diameters less than 500 nm may be produced from dilution of PEC precursor solutions with aqueous solutions that comprise surfactants and adjuvants designed to deliver a desired pH in the diluted solutions.

The target pH of the diluted solutions was near neutral (pH 6-7) to slightly acidic, and the PECs comprise DADMAC as the cationic polyelectrolyte and PAA as the anionic polyelectrolyte. Thus, the carboxylic acid groups of PAA will be in the fully ionized, anionic form, i.e., the pH of the diluted solutions is significantly higher than the estimated pKa of the carboxylic acid groups, or about 4. PEC precursor solutions formulated with R values >1.0 produce PECs with cationic (positive) zeta potential values upon dilution with aqueous systems that do not comprise surfactants, as discussed herein.

The results for formulations DPQ1 and DPQ2 in Table 6.2 show that PECs with cationic zeta potential values are produced upon dilution with aqueous systems comprising cationic surfactants, in this case, cationic germicides. In addition, the PECs produced by dilution of the precursor solutions with aqueous systems comprising surfactants are very similar in size and zeta potential, and are not significantly affected by the manner of dilution. Sample DPQ1 was diluted by adding an aqueous quat solution to the PECs precursor solution, while sample DPQ2 was made by adding the PECs precursor solution to an aqueous quat solution. Inventors believe, without being bound by theory, that the results indicate that because the PECs being produced and the aqueous micelles of the surfactant being produced upon dilution are of the same net charge (cationic), there is electrostatic repulsion between the PECs and the micelles, which minimizes or eliminates interactions between them, and hence PECs will rapidly assemble upon dilution of PEC precursor solutions.

The results in Table 6.2 (sample DPSLS1) also indicate that PEC precursor solutions formulated at R values <1.0 (here at R=0.5), in order to deliver PECs with anionic (negative) zeta potential values, may be diluted with aqueous solutions comprising anionic surfactants. Thus, for the reasons discussed above, stable PECs of suitable Z-average diameter and anionic charge are observed in the final dilution of sample DPSLS1.

When the aqueous solution used for dilution of a PEC precursor solution comprises a nonionic surfactant or an amphoteric surfactant such as an amine oxide in an aqueous solution with a pH adjusted such that the surfactant exhibits no charge (in this case an amine oxide near pH 7), little electrostatic interaction between the surfactant molecules or micelles and the PECs would be expected. The results in Table 6.2 show (samples DPAO1 and DPAO2) that PEC precursor solutions deliver stable PECs of appropriate Z-average diameter when they are diluted with an aqueous solution comprising an uncharged amine oxide (nonionic surfactant). The results also show that the net charge on the PECs produced via dilution can be controlled via the R parameter of the precursor solution, i.e, PECs with anionic charge (negative zeta potential) are produced with R values <1.0 and PECs with cationic charge (positive zeta potential) are produced with R values >1.0.

Example 7

Compositions and Characterization of PECs Prepared Via Dilution of Precursor Solutions with Aqueous Solutions of Germicides Aqueous solutions comprising stable PECs produced via the present invention may be used to modify the properties of both hard surfaces (glass, tile, porcelain, metals and the like) as well as soft surfaces like fabrics, nonwoven or woven, paper, or fibers of any type, through the rapid adsorption of PECs onto such surfaces. It is also possible to provide extended antimicrobial properties to such surfaces through the adsorption of PECs that comprise an antimicrobial agent such as a germicidal quat, a non-polymeric biguanide such as chlorhexidine or alexidine, or a metal ion such as silver, copper and the like.

Inventors believe, without being bound by theory, that stable PECs comprising such antimicrobial agents are able to anchor the antimicrobial agents to said surfaces. Thus, in a single step process, the surface is exposed to an aqueous solution comprising PECs. The antimicrobial agent not only provides disinfection during the exposure, but also imparts extended or residual antimicrobial properties to the surface. Alternatively, said surfaces may be treated in a two-step process comprising exposing the surface to an aqueous solution of stable PECs, followed by exposure to a second aqueous solution comprising the antimicrobial active, whereby the active becomes anchored to the PEC layer established on the surface during the first exposure.

TABLE 7.1

Compositions of PEC Precursor Solutions for Dilution with Aqueous Solutions Comprising Surfactants

| Formulation Name | Precursor sample | Precursor, grams | Water, grams | BTC 1010, grams | BTC 1010 stock concentration | NaOH, grams | Total polymer concentration, mM | R value | Succinic Acid, mM | BTC 1010, wt % | pH of final solution | Precipitate | Comments - |
|---|---|---|---|---|---|---|---|---|---|---|---|---|---|
| DPQ 3 | DADPAA 9 | 0.19 | 49.6 | 0.20 | 5 wt % | 2.6 | 1.5 | 0.5 | 1.0 | 0.02 | 6.03 | No | NaOH added to quat solution, no pH adjustment, PECs into quat |
| DPQ 4 | DADPAA 9 | 0.39 | 96.33 | 1.00 | 40 wt % | 2.5 | 1.5 | 0.5 | 1.0 | 0.4 | 5.21 | No | Higher quat level, NaOH added to quat solution |
| DPQ 5 | DADPAA 9 | 0.41 | 96.15 | 1.01 | 40 wt % | 3.0 | 1.5 | 0.5 | 1.0 | 0.4 | 7.18 | No | Quat into PECs, pH adjusted |

TABLE 7.2

Characterization of PECs Made Via Dilution of Precursors

| Formulation Name | R value | Total Polymer concentration, mM | Z-average diameter, nm | Zeta Potential, mV | Comments |
|---|---|---|---|---|---|
| DPQ3 | 0.5 | 1.5 | 142.6 | +37.8 | PECs into quat soln, 0.02% BTC1010 |
| DPQ4 | 0.5 | 1.5 | 191.5 | +56.9 | PECs into quat 0.4% BTC1010 |
| DPQ5 | 0.5 | 1.5 | 376.1 | +51.8 | Quat into PECs - 0.4% BTC1010 |

The results in Table 7.2 show that stable PECs may be produced by dilution of a PECs precursor solution with an aqueous solution comprising a surfactant. The PEC precursor solution was formulated with the R value <1.0, in order to produce PECs with an anionic charge which would have a strong electrostatic interaction with the cationic surfactant, here a germicidal quat, present in the aqueous solution used to dilute the PECs precursor solution. Thus, the zeta potentials of the stable PECs produced via dilution are cationic (positive), that is, "charge reversed" relative to the R parameter of the precursor solution. Inventors believe, without being bound by theory, that the stable PECs produced are "decorated" with quat molecules through interactions of the cationic headgroups of the quats and the ionized carboxylate groups of the PAA comprising the PEC.

Thus, stable PECs may be produced via dilution of the precursor solutions of the instant invention, even if the aqueous diluent solution comprises a surfactant of opposite charge to the net charge of the PECs which would be produced in the absence of the surfactant, where said charge of the PECs can be controlled by adjusting the R parameter. As shown in the examples, the concentration of the quat in the final diluted aqueous solution may be adjusted, depending on the antimicrobial and surface modification performance and kinetics desired.

This example also illustrates another method for controlling the zeta potential of the PECs of the instant invention, i.e. through "decoration" with soluble surfactants of net opposite charge to the PECs. The PECs are rapidly assembled during the dilution step with sizes appropriate for colloidal stability (<500 nm Z-average diameter) in a single step, eliminating any need for isolation and further mechanical manipulation, for example through high shear mixing, allowing for the direct use of the dilute final solution comprising the decorated PECs for treatment of a surface to modify its properties.

Example 8

Compositions and Characterization of PECs Prepared Via Dilution of Precursor Solutions with Aqueous Solutions of Surfactants in Multiple Steps Stable PECs may be produced via dilution of PEC precursor solutions of the instant invention, even when the diluent used comprises surfactants, and even if the relative charges of the surfactant in the diluent solution and the PECs produced via manipulation of the R parameter are opposites. Thus, "decorated" and "charge-reversed" PECs, which can be useful for controlling the modification of surfaces, and for anchoring antimicrobial compounds such as quats and biguanides onto surfaces to provide extended antimicrobial properties may be produced.

Decorated or charge-reversed PECs may also be produced in multiple step processes. Thus, a PEC precursor composition shown in Table 8.1 was designed to yield PECs with a net anionic charge upon dilution with an aqueous solution comprising an amine oxide surfactant. In this example, stable PECs were produced by adding an amine oxide solution to the precursor solution, with simple agitation provided by a magnetic stirbar. The characteristics of the PECs produced via this first dilution are shown in Table 8.2.

A subsample (9 ml) of formulation DPAO3 was added to a vial with a magnetic stirbar. To this subsample, 1 ml of an aqueous solution of BTC1010 (0.2%) was added with stirring, to produce a clear solution free of coacervates and precipitates containing the PECs and the germicidal quat at 0.02%. The characteristics of the PECs in this final dilute solution (sample DPAOQ1) are also shown in Table 8.2.

TABLE 8.1

Composition of PEC Precursor Solution For Dilution With Aqueous Solutions Comprising Surfactants in Two Steps

| Formulation Name | Precursor sample | Precursor, grams | Water, grams | Ammonyx LO, grams | Ammonyx LO stock concentration | Total polymer concentration, mM | R value | Succinic Acid, mM | Ammonyx LO, wt % | Precipitate |
|---|---|---|---|---|---|---|---|---|---|---|
| DPAO3 | DADPAA 9 | 0.13 | 31.05 | 2.2 | 0.3 wt % | 1.5 | 0.5 | 1.0 | 0.02 | No |

TABLE 8.2

Characterization of PECs Produced Via Dilution of PECs Precursor Solutions

| Formulation Name | R Value | Total Polymer concentration, mM | Z-average diameter, nm | Zeta Potential, mV | Comments |
|---|---|---|---|---|---|
| DPAO3 | 0.5 | 1.5 | 209.7 | −45.8 | LO into PECs - no salt, original dilution |
| DPAOQ1 | 0.5 | 1.35 | 211.4 | +36.1 | 0.2% BTC1010 added to above |

Notes -
diameters reported are average of four replicate analyses of the same sample. Zeta potential values are the averages of duplicate analyses of the same sample The results in Table 8.2 show that stable PECs of appropriate size and with a net anionic charge (negative zeta potential) can be produced via dilution of PECs precursor solution with an aqueous solution comprising an amine oxide at pH near neutral. The rapid assembly of the PECs via the dilution of appropriate precursor solutions prevents the formation of precipitates or coacervates due to interactions between the surfactant micelles and the PECs during the assembly process.

The results in Table 8.2 also show that stable PECs of net anionic charge (negative zeta potential) may be further diluted with a surfactant solution comprising a cationic surfactant, here a germicidal quat, in order to produce stable PECs that are decorated with the quat molecules via electrostatic interactions. These interactions result in the reversal of charge of the PECs, allowing PECs produced from precursor solutions formulated at R=0.5 to exhibit a cationic zeta potential. Such decorated PECs are useful in the subsequent modification of surfaces, since germicidal quats may be anchored onto surfaces in this manner.

Example 9

Compositions and Characterization of PECs Prepared Via Dilution of Precursor Solutions with Alkaline Sodium Hypochlorite The PEC precursor solutions may comprise a concentrated solution of sodium hypochlorite (8.25%, for example), which is added to laundry by the household consumer via direct addition to the wash water, or through the use of an automated dosing reservoir for the hypochlorite bleach that is provided by many washing machine manufacturers. A typical dose rate of bleach in a home washing is about 2 cup for a top-loading washer containing 69 liters of water. Thus, the PEC precursor solutions with hypochlorite are designed to produce PECs in the wash water when diluted by a factor of about 583 (583:1).

Table 9.1 summarizes the compositions of PEC precursor compositions with sodium hypochlorite which can deliver PECs of various R values when diluted in water by a factor of 583.

TABLE 9.1

PEC Precursor Compositions Comprising Concentrated Sodium Hypochlorite (and Controls)

| Formulation Name | DADMAC, grams | PAA, grams | NaOCl, grams | NaOH, grams | NaCl, grams | Water, grams | DADMAC, wt % | PAA, wt % | Total polymer concentration, mM | pH | R value | Precipitate | Comments |
|---|---|---|---|---|---|---|---|---|---|---|---|---|---|
| DADPAA 21 | 0.50 | 1.45 | 38.16 | — | — | 7.33 | 0.42 | 0.74 | 130 | 12.64 | 0.25 | No | |
| DADPAA 22 | 7.85 | 10.72 | 343.48 | — | — | 72.49 | 0.70 | 0.62 | 130 | 12.64 | 0.50 | No | |
| DADPAA 23 | 1.10 | 1.03 | 38.17 | — | — | 8.27 | 0.90 | 0.53 | 130 | 12.55 | 0.75 | No | |
| DADPAA 24 | 12.62 | 6.80 | 343.46 | — | — | 76.16 | 1.20 | 0.40 | 130 | 12.64 | 1.33 | No | |
| DADPAA 25 | 1.72 | 0.61 | 38.19 | — | — | 8.64 | 1.40 | 0.31 | 130 | 12.59 | 2.0 | No | |
| DADPAA 26 | 18.97 | 3.29 | 343.45 | — | — | 79.73 | 1.67 | 0.19 | 130 | 12.67 | 4.0 | No | |
| DADPAA 27 | 0.85 | 1.19 | — | 3.23 | 6.49 | 37.00 | 0.70 | 0.62 | 130 | 12.48 | 0.50 | No | no hypo control |
| DADPAA 28 | 2.11 | 0.37 | — | 2.01 | 6.50 | 36.03 | 1.67 | 0.19 | 130 | 12.45 | 4.0 | No | no hypo control |
| PAA 1 | — | 1.78 | 38.18 | 2.60 | — | 7.47 | — | 0.92 | 130 | 12.52 | — | No | PAA only control |
| DADMAC 1 | 2.01 | — | 38.18 | — | — | 9.20 | 2.09 | — | 130 | 12.69 | — | No | DADMAC only control |

Notes:
DADMAC (Floquat 4540, SNF Inc., aqueous solution with 40% polymer actives), PAA (Aquatreat AR4, Akzo Nobel, aqueous solution with 26% polymer actives), NaOCl (aqueous solution containing 10.8 wt % sodium hypochlorite and 8.5 wt % sodium chloride), NaOH (1.0M aqueous solution), NaCl (solid granules, 100% actives).

Table 9.2 summarizes the characterization of the diameters and the zeta potentials of the PECs produced from the precursor solutions described above. The samples were prepared by adding 30.9 microliters (via adjustable pipet) to 18.0 milliliters of water contained in a 20 ml capped vial. The solutions were gently mixed by brief shaking of the capped vial, and then a 1 ml sample was removed and loaded into either a disposable scattering cuvette or into the disposable zeta potential cell used with the Malvern Zetasizer. The water used for dilution was either deionized or was synthetic hard water containing 100 ppm total hardness ions. Due to the significant dilution of the precursor solutions of this example, it is believed that the mean zeta potentials of the PECs formed by dilution may be measured in the presence of the sodium hypochlorite.

TABLE 9.2

Compositions and Characterization of PECs Produced Via Dilution of Precursor Compositions from Table 9.1

| Formulation Name | Precursor Composition | Precursor, µL | Water, mL | Hard water, mL | DADMAC, mM | PAA, mM | Total polymer concentration, mM | R value | Z-average diameter, nm | Zeta potential, mV |
|---|---|---|---|---|---|---|---|---|---|---|
| DADPAA 29 | DADPAA 21 | 30.9 | 18.0 | — | 0.3 | 1.2 | 1.5 | 0.25 | 170.7 | Not measured |
| DADPAA 30 | DADPAA 21 | 30.9 | — | 18.0 | 0.3 | 1.2 | 1.5 | 0.25 | 204.6 | Not measured |
| DADPAA 31 | DADPAA 22 | 30.9 | 18.0 | — | 0.5 | 1.0 | 1.5 | 0.50 | 218.0 | −45.9 |
| DADPAA 32 | DADPAA 22 | 30.9 | — | 18.0 | 0.5 | 1.0 | 1.5 | 0.50 | 640.6 | −9.58 |
| DADPAA 33 | DADPAA 23 | 30.9 | 18.0 | — | 0.64 | 0.86 | 1.5 | 0.75 | 269.0 | Not measured |
| DADPAA 34 | DADPAA 23 | 30.9 | — | 18.0 | 0.64 | 0.86 | 1.5 | 0.75 | 551.3 | Not measured |
| DADPAA 35 | DADPAA 24 | 30.9 | 18.0 | — | 0.86 | 0.64 | 1.5 | 1.33 | 222.2 | +55.2 |
| DADPAA 36 | DADPAA 24 | 30.9 | — | 18.0 | 0.86 | 0.64 | 1.5 | 1.33 | 207.6 | +49.8 |
| DADPAA 37 | DADPAA 25 | 30.9 | 18.0 | — | 1.0 | 0.5 | 1.5 | 2.0 | 182.8 | +51.0 |
| DADPAA 38 | DADPAA 25 | 30.9 | — | 18.0 | 1.0 | 0.5 | 1.5 | 2.0 | 224.9 | +48.2 |
| DADPAA 39 | DADPAA 26 | 30.9 | 18.0 | — | 1.2 | 0.3 | 1.5 | 4.0 | 192.9 | +56.7 |
| DADPAA 40 | DADPAA 26 | 30.9 | — | 18.0 | 1.2 | 0.3 | 1.5 | 4.0 | 218.9 | +46.8 |
| DADPAA 41 | DADPAA 27 | 30.9 | — | 18.0 | 0.5 | 1.0 | 1.5 | 0.5 | 551.8 | Not measured |
| DADPAA 42 | DADPAA 28 | 30.9 | — | 18.0 | 1.2 | 0.3 | 1.5 | 4.0 | 323.9 | Not measured |
| PAA 2 | PAA 1 | 30.9 | — | 18.0 | — | 1.5 | 1.5 | — | | Too dilute to measure |
| DADMAC 2 | DADMAC 1 | 30.9 | — | 18.0 | 1.5 | — | 1.5 | — | | Too dilute to measure |
| PAA1 | — | — | — | — | — | 130 | 130 | — | 32.3 | Not measured |
| DADMAC1 | — | — | — | — | 130 | — | 130 | — | 19.2 | Not measured |

Notes:
Synthetic hard water contained 100 ppm hardness as $Ca^{+2}/Mg^{+2}$ in mole ratio of 3:1.

The results in Table 9.2 indicate that stable PECs are formed by dilution in deionized water of the PEC precursor solutions comprising sodium hypochlorite over a wide range of R values, i.e. from 0.25 to 4.0. The results also indicate that the PECs formed by dilution in deionized water exhibit negative mean zeta potentials when the R value of the precursor solution is less than 1, and exhibit positive mean zeta potentials when the R value of the precursor solutions are greater than 1, which is expected for this example since the pH of the precursor solutions is high (designed to be greater than 12.0), which ensures full ionization of the carboxylic acid groups of the poly(acrylic acid) incorporated into the PECs. As discussed herein, control of the zeta potential of PECs comprising poly(acrylic acid) and like polymers made via dilution from precursor solutions is possible through variation of the pH of the precursor solution and/or the pH of the final diluted solution comprising the PECs.

The results in Table 9.2 also indicate that stable PECs are formed by dilution in hard water of the PECs precursor solutions comprising sodium hypochlorite at R values of less than 0.5, and also at R values greater than 1.0. At R=0.50 and R=0.75 of the precursor solutions, the diameters of the PECs formed by dilution in hard water are significantly larger than in the case of dilution in deionized water (see examples DADPAA 32 and DADPAA 34). Inventors believe, without being bound by theory, that binding of significant amounts of divalent ions present in the hard water (for example, $Ca^{+2}$ and $Mg^{+2}$ ions) to the PECs formed by dilution of the precursors can occur. Evidence for this binding includes the cationic (positive) shift in the zeta potential of the PECs formed by dilution of the precursor solution with R=0.5 in deionized water (mean zeta=−45.9) to a value of −9.58 in hard water.

The results in Table 9.2 also show that stable PECs of suitably small diameter can be formed by dilution of PECs precursor solutions in hard water when the R values of the precursor solutions comprising hypochlorite are >1.0.

The results in Table 9.2 also show that stable PECs are formed by dilution in hard water of PECs precursor solutions in which sodium chloride has been substituted for the sodium hypochlorite on a molar basis. Thus, Examples DADPAA41 and DADPAA42 show that PECs are formed by dilution of precursor solutions comprising high electrolyte levels (2.2 M NaCl). As discussed herein, incorporation of electrolytes in the precursor solutions can be helpful, and can be adjusted to provide clear, stable precursor solutions which can deliver PECs of controlled size and charge upon dilution.

Analysis of two control formulations (PAA2 and DADMAC2) comprising hypochlorite and a single polymer was not possible when the formulations were diluted in the same manner as the PEC precursor solutions, due to the very low level of light scattering by the soluble polymer chains in solution. Those skilled in the art will recognize this limitation as being due to the much smaller overall size of the soluble polymer chains when they are not incorporated into PECs, and to the fact that the absolute levels of light scattering in DLS experiments will scale with the diameter of the scattering particles to the sixth power, i.e., scattering is proportional to $(diameter)^6$. Thus, the neat control formulations PAA1 and DADMAC1 were instead analyzed. The increased concentration of the polymers in these formulations (130 mM) yielded enough light scattering for the determination of the average diameters of the soluble polymer chains, which were confirmed to be much smaller than that of the PECs made by dilution of the precursor solutions, as expected.

TABLE 9.3

Hypochlorite (Concentration in PEC Solutions from Table 9.1 Remaining in Solution when Incubated at 49° C.

| Formulation Name | Total polymer concentration, mM | R value | Hypochlorite Concentration in Solution Incubated at 49° C., wt % | | | | |
|---|---|---|---|---|---|---|---|
| | | | Initial value | Day 7 | Day 14 | Day 21 | Day 28 |
| DADPAA 26 | 130 | 4.00 | 8.1 | 4.9 | 3.5 | 0.4 | 0.0 |
| DADPAA 25 | 130 | 2.00 | 8.3 | 5.2 | 3.6 | 2.7 | 2.1 |
| DADPAA 24 | 130 | 1.33 | 8.4 | 5.2 | 3.7 | 2.0 | 2.1 |
| DADPAA 23 | 130 | 0.75 | 8.2 | 5.1 | 3.7 | 2.8 | 2.4 |
| DADPAA 22 | 130 | 0.50 | 8.1 | 5.1 | 3.6 | 2.3 | 2.5 |
| DADPAA 21 | 130 | 0.25 | 8.2 | 5.2 | 3.7 | 2.8 | 2.3 |
| PAA 1 | 130 | — | 8.2 | 5.2 | 3.8 | 2.9 | 2.3 |
| DADMAC 1 | 130 | — | 8.5 | 5.1 | 0.3 | 0.0 | 0.0 |

Spores (or more properly, endospores) are a type of dormant cell produced by many types of bacteria, such as *Bacillus* and *Clostridium*, in response to stressful environmental conditions. The exterior coats of spores, which are responsible for the resistance to extreme conditions, are multi-layer structures composed primarily of cross-linked polypeptides. When a spore encounters an environment favorable for growth of vegetative cells, the spore coat allows passage of nutrients and water to the spore, and the production of a vegetative cell, in a germination process.

The compositions of the polypeptides, proteins, and other minor materials that make up the coat of *Bacillus subtilis* spores, for example, result in the spore exhibiting a net anionic charge (negative zeta potential) when the spores are dispersed in water at neutral pH, i.e., pH 7. Polypeptides in aqueous solutions will exhibit a net charge as a function of pH of the solution that is determined by the relative numbers of anionically and cationically charged amino acids in the polypeptide chain. At a pH corresponding to the isoelectric point of a polypeptide, the net charge on the polypeptide is zero, due to the presence of equal numbers of cationically charged and anionically charged amino acids. The net charge on the polypeptide at pH values greater than the isoelectric point will thus be negative (anionic), and will be positive (cationic) at pH values below the isoelectric point. The isoelectric points (or point of zero charge) of various *Bacillus* spores have been found to lie between about pH 3 and pH 4. Thus, the zeta potential of the spores used herein was found to be cationic (positive) when the spores were dispersed in water adjusted to around pH 2, i.e., well below the known isoelectric point.

*Bacillus* spores exhibit average diameters of around 1000 nm (1 micrometer), and can thus act as charged scattering particles when dispersed in aqueous media. Measurements of the zeta potential of spores are thus readily accomplished using the approach of laser Doppler velocity determination that is implemented in modern instruments, such as the Malvern Zetasizer. Those skilled in the art will realize that an appropriate concentration of spores for such measurements of the zeta potential of the spores can readily be determined, using dilutions of standard dispersions of spores which are commercially available. Typically, the spore concentrations in these standard dispersions are expressed as spores/ml or colony forming units/ml of the dispersions. Inventors have found that reproducible measurements of the zeta potential of *Bacillus* spores can easily be made at spore concentrations of around 1 to $3.3 \times 10^6$ spores/ml. Such concentrations are readily made by dilution of commercially available stocks with concentrations of $1 \times 10^8$ spores/ml.

Spores contaminating surfaces such as towels or laundry or hard surfaces such as floors, walls, medical equipment, food preparation or service counters, etc. will germinate and grow, producing increasing numbers of organisms on the surface, when the environment becomes favorable, for example, when the surface becomes soiled or contaminated with materials that are suitable nutrients for the microorganisms. Germicidal quaternary ammonium compounds or biguanides or certain cationic polymers, such as chitosan, have little effect on dormant spores, but if they are present on the surface of the spores in sufficient concentration, they can kill the organism at the initial stage of germination when the environmental conditions become favorable.

During the cleaning of surfaces potentially contaminated with spores, especially in healthcare facilities, it is critical that spores are efficiently removed by the rag, mop, wipe cloths or other cleaning implements used to contact the cleaning solution with the surfaces. The surface charge on the majority of cleaning implements is negative (anionic) zeta potential, and hence have a tendency to electrostatically repel any spores, which also have a native negative (anionic) zeta potential. Cleaning solutions comprising PECs, which will rapid adsorb onto the surfaces of the spores and thus increase the zeta potential to positive (cationic) values can aid in the efficiency of the mechanical removal of the spores from the surfaces and aid in the retention of the spores on or in the cleaning implement, thus preventing mechanical re-spreading of the spores to other surfaces.

In some applications, such as the use of spores as bio-insecticides, bio-fungicides, or bio-control agents, as foliar sprays or seed coatings, the increased adhesion of spores to the surfaces of seeds or crops should be combined with low spore toxicity, in order to ensure a net increase in efficiency of the process. Thus, the polyelectrolytes selected for assembly into the PECs, and especially the cationic polyelectrolyte, must show little or no toxicity to the vegetative form of the cells resulting from the germination of the spores, and must show little or no tendency to inhibit the germination rates of the spores upon use in the field.

Example 10

Modification of the Zeta Potential of *Bacillus* Spores Via Interactions with PECs Produced by the Dilution of PECs Precursor Solutions In order to demonstrate the utility of PECs for the modification of the surface charge of microorganisms, the zeta potentials of *Bacillus subtilis* spores dispersed in aqueous solutions of PECs produced from dilution of PEC precursor solutions were measured.

Dispersions of the spores in water or in aqueous solutions comprising PECs at spore concentrations of at least $1 \times 10^6$ were all prepared in the same manner. Ten microliters of a fresh commercially available dispersion of *Bacillus subtilis* spores (spore concentration of $1 \times 10^8$ spores/ml) were added to 990 microliters of water or aqueous solution comprising PECs, gently mixed by drawing into and expelling from a manually operated pipette with a disposable tip, followed by loading of the entire sample into a disposable capillary zeta potential measurement cell.

PEC precursor solutions with values of the R parameter both less than and greater than 1.0, which were clear and free of coacervates and precipitates were prepared with compositions summarized in Table 10.1. The precursor solutions were then diluted in a first step to provide aqueous solutions comprising PECs of both net anionic charge (R parameter<1) and net cationic charge (R parameter>1) all at the same total polymer concentration of 1.5 mM.

In order to demonstrate the effect of the concentration of PECs made in this manner on the zeta potential of *Bacillus* spores, serial dilutions of the samples of PECs made at 1.5 mM were also made with deionized water.

and other minor components of the spore coat. The isoelectric points (or point of zero charge) of various *Bacillus* spores are known to lie between about pH 3 and pH 4. Thus, the zeta potential of the spores used herein was found to be cationic (positive), when the spores were dispersed in water adjusted to around pH 2 (Control 2), i.e., well below the known isoelectric point.

The results in Table 10.2 show that the zeta potential of the spores can be adjusted by exposing the spores to aqueous solutions comprising PECs made via dilution of precursor solutions. The PECs made via dilution of PDS1, formulated with an R value of 0.5 will exhibit a net negative zeta potential, but are capable of adsorbing, and hence modifying, surfaces such as silica that also exhibit a net negative charge at a given pH. Inventors believe, without being bound by theory, that the stable PECs of the instant invention have enough cationic charges (here due to the DADAMC of the PECs) readily available to the anionic sites on solid surfaces to drive adsorption of the PECs onto the solid surfaces. Alternatively they may be sufficiently flexible or capable of structural changes at solid surfaces such that adsorption of the PECs, which exhibit a net negative (anionic) zeta potential, readily occurs on surfaces which also have a net negative charge, such as silica at pH 7.0.

TABLE 10.1

Compositions of PEC Precursor Formulations Used to Deliver Aqueous Solutions of PECs for the Modification of the Surfaces of *Bacillus* Spores

| Formulation Name | Precursor sample | Precursor, grams | Water, grams | Total polymer concentration, mM | DADMAC, mM | PAA, mM | R value | pH |
|---|---|---|---|---|---|---|---|---|
| PDS1 | DADPAA 9 | 0.41 | 99.6 | 1.6 | 1.05 | 0.52 | 0.5 | 7.04 |
| PDS2 | DADPAA 10 | 0.47 | 99.6 | 1.8 | 1.45 | 0.36 | 4.0 | 7.03 |

Notes:
DADMAC (Floquat 4540, SNF Inc., aqueous solution with 40% polymer actives), PAA (Aquatreat AR4, Akzo Nobel, aqueous solution with 26% polymer actives),

TABLE 10.2

Characterization of *Bacillus Subtilis* Spore Dispersions Containing at Least $1 \times 10^6$ spores/ml in Absence and Presence of PECs Prepared from Precursor Solutions

| Formulation Name | R value | Total Polymer concentration, mM | Zeta Potential of Spore, mV | Comments |
|---|---|---|---|---|
| Control 1 | — | — | −27.4 | Spores only dispersed in water, pH 7 |
| Control 2 | — | — | +12.4 | Spores only dispersed in 0.01N HCl, pH 2 |
| PDS1 | 0.5 | 1.5 | −51.5 | Spores with PECs produced from dilution of precursor solution |
| PDS1A | 0.5 | 0.15 | −44.8 | Spores with PECs serially diluted from PDS1 |
| PDS1B | 0.5 | 0.015 | −42.0 | Spores with PECs serially diluted from PDS1 |
| PDS1C | 0.5 | 0.0015 | −47.3 | Spores with PECs serially diluted from PDS1 |
| PDS2 | 4.0 | 1.5 | +31.6 | Spores with PECs produced from dilution of precursor solution |
| PDS2A | 4.0 | 0.15 | +27.0 | Spores with PECs serially diluted from PDS2 |
| PDS2B | 4.0 | 0.015 | +15.3 | Spores with PECs serially diluted from PDS2 |
| PDS2C | 4.0 | 0.0015 | +7.03 | Spores with PECs serially diluted from PDS2 |
| PDS2D | 4.0 | 0.0015 | +6.45 | Spores with PECs serially dilated from PDS2 |

Notes -
zeta potential values are averages of at least 2 replicate measurements. The precision of replicate measurements is estimated as 10% relative or better by the instrument manufacturer.

The results in Table 10.2 (Control 1) indicate that the zeta potential of the spores dispersed in water at neutral pH is found to be negative (anionic charge), which is expected. The anionic charge on the spores at neutral pH is thought to be due primarily to the composition of the polypeptides, proteins, Thus, the zeta potential of the spores exposed to PECs made at R=0.5 (formulation PDS1) is significantly more anionic (more negative) than that of the control spores, due to the adsorption of PECs onto the spore surfaces. Inventors believe, without being bound by theory, that the cationic sites of the PECs are readily available for electrostatic interactions with the negative sites on the spore coat surface, and hence the PECs are rapidly adsorbed onto the spores. A reduction in the number of anionic sites on the spore surface (at neutral pH, i.e., well above the isoelectric point of the spore) through "neutralization" by adsorption of a cationic species, such as a cationic germicide surfactant, would be expected to shift the zeta potential of the spore in a positive direction, i.e., toward less negative values. Surprisingly, adsorption of PECs with a net negative zeta potential (at R=0.5 here) delivers significant numbers of anionic (negative) charges, due to the ionized carboxylate groups of the PAA of the PECs to the spore surface, more than compensating for the loss of anionic charges due to interactions between the spore surface and the cationic charges of the DADMAC of the PECs. Thus, the zeta potential of the spores due to modification by the PECs is shifted in an anionic (negative) direction.

The results in Table 10.2 also show that the zeta potential of the same number of spores may be adjusted by adsorption of PECs with a net negative charge over a very wide range of PEC concentrations. Even at the extremely low concentration of PECs (expressed as total polymer concentration) of 0.0015 mM, the zeta potential of the spores may be adjusted to values significantly more negative than that of the native spores at the same pH. Thus, the adsorption of PECs for the modification of spores is a very effective and simple approach. Those skilled in the art will realize that the use of PECs for the modification of surfaces advantageously overcomes the limitations of the use of ordinary surfactants for surface modification.

For example, it is well known that the adsorption of surfactants onto surfaces is drastically reduced when the surfactant concentration in the aqueous solution is decreased below the critical micelle concentration of the given surfactant, due to the equilibrium distribution of surfactant molecules between micelles, monomeric surfactant, the solid-liquid and the air-liquid interfaces. Since the PECs of the instant invention do not exhibit a critical micelle concentration like surfactants do, their adsorption onto solid surfaces of all types, including microorganisms, is extremely efficient. Also, unlike surfactants, the PECs of the instant invention may not be efficient at lowering the surface tension of water, but can, like surfactants, improve the wetting and spreading of aqueous solutions on surfaces through their adsorption onto the surfaces, which can modify the surfaces directly, increasing their affinity for water.

In addition, since the net negative PECs present in formulation PDS1 were made via the dilution of PECs precursor solutions of the instant invention, a very wide range of dilution factors, with the advantages of using "concentrates" to treat large volumes of solutions comprising microbes (for example, bacterial spores) may be readily accomplished.

The results in Table 10.2 also show that the zeta potential of spores may be adjusted to positive values through exposure to PECs exhibiting a net positive charge. Exposure of the spores to aqueous solutions comprising PECs made via dilution of precursor solutions formulated at a value of the R parameter greater than 1.0 (here 4.0) results in adsorption of the PECs onto the spores, resulting in a shift of the zeta potential of the spores from −27.4 (control spores) to +31.6, even though the pH of the aqueous solution is neutral, about pH 7, which is well above the isoelectric point of the spores. Inventors believe, without being bound by theory, that the significant increase in zeta potential of the spores is due to adsorption of PECs that leads to overcompensation of charges on the spore surface, and hence a large increase in the zeta potential. The data also show that the zeta potential of the spores may be adjusted to values even more positive (cationic) than that of the native spores well below their isoelectric point (point of zero charge). Thus, the zeta potential of the spores in water at pH 2 is found to be +12.4, while in the presence of net cationic PECs (R=4) at pH 7, the zeta potential is +31.6, i.e., "overcompensated", as explained above.

The results in Table 10.2 also show that, for the same number of spores, a reduction in the concentration of the PECs (expressed as total polymer concentration) to 0.0015 mM still results in the modification of the zeta potential of the spores in the positive (cationic) direction. At 0.0015 mM total polymer concentration, the zeta potential of the spores was found (for two independent preparations of modified spores) to be +7.03 and +6.45, well above the native value of the spores in water at pH 7, which was −27.4. Thus, as described above, a very wide range of dilution factors, with all of the advantages of the design of "concentrates" capable of delivering PECs mentioned above, are also available for the modification of spore surface charges in the positive (cationic) direction.

Example 11

Modification of the Zeta Potential of Bacillus Spores Via Interactions with PECs Produced by the Dilution of PEC Precursor Solutions in Multiple Steps As described above, the zeta potential of spores may be adjusted to more negative values by exposure to PECs of net anionic charge. In this example, sample DPAO3 was used to modify the surfaces of spores. Sample DPAO3 comprised PECs of anionic charge made via dilution of a precursor solution with a surfactant solution comprising an amine oxide. The same number of spores were modified by exposure to the charge-reversed PECs in sample DPAOQ1, which comprised the PECs, an amine oxide and a germicidal quat. In addition, in a demonstration of an alternative process, the spores which had been modified by the adsorption of the anionic PECs from formulation DPAO3 were further modified by the addition of an aqueous solution (100 microliters of BTC1010 in water at 0.2%) of the germicidal quat to 900 microliters of the spore dispersion, to yield the same total polymer and quat concentration (0.02%) as was present in the spore dispersion treated in one step.

TABLE 11.1

Characterization of Bacillus Subtilis Spore Dispersions Containing At least 1 × $10^6$ spores/ml in Absence and Presence of PECs Prepared from Precursor Solutions

| Formulation Name | R value | Total Polymer concentration, mM | Zeta Potential of Spore, mV | Comments |
| --- | --- | --- | --- | --- |
| Control 1 | — | — | −27.4 | Spores only dispersed in water, pH 7 |
| Control 2 | — | — | +12.4 | Spores only dispersed in 0.01N HCl, pH 2 |

TABLE 11.1-continued

Characterization of *Bacillus Subtilis* Spore Dispersions Containing At least 1 × $10^6$ spores/ml in Absence and Presence of PECs Prepared from Precursor Solutions

| Formulation Name | R value | Total Polymer concentration, mM | Zeta Potential of Spore, mV | Comments |
|---|---|---|---|---|
| DPAO3 | 0.5 | 1.5 | −44.8 | Spores with PECs produced from dilution of precursor solution |
| DPAO3A | 0.5 | 1.35 | +34.6 | Quat added to subsample of Spores modified by DPAO3 |
| DPAOQ1 | 0.5 | 1.35 | +36.3 | Spores with charge-reversed decorated PECs |

The results shown in Table 11.1 indicate that the zeta potential of the spores modified by exposure to the PECs in sample DPAO3 was negative, as expected. Since sample DPAO3 comprises stable PECs and an amine oxide surfactant, it also serves as an example of a ready to use hard surface cleaner that comprises PECs that could be used to modify the surfaces of spores. The results also indicate that the addition of quat to the same spore dispersion in a second step (sample DPAO3A) results in adsorption of a significant amount of quat to the modified spore surface, resulting in a reversal of the spore zeta potential to positive (cationic). The results also indicate that the modification of the spore surfaces through adsorption of charge-reversed decorated PECs may be accomplished in a single step, (sample DPAOQ1) resulting in reversal of the spore zeta potential to a very similar, positive value.

The results also indicate that the PECs of the instant invention may be used to modify the surfaces of microbes, such as bacterial spores as used here, including the anchoring of a germicidal quat. The anchoring of the germicidal quat may be accomplished with a single exposure of the spores to an appropriate solution of PECs, or may be accomplished in a two-step process, wherein a PEC of net anionic charge is first adsorbed onto the spores, followed by exposure of the modified spores to an aqueous solution comprising the germicidal quat which causes adsorption or anchoring of the quat onto the spore surface.

Example 12

Nontoxic Surface Modification of *Bacillus subtilis* Spores

In order to increase the adhesion of beneficial spores to seeds or crop surfaces bearing native anionic (negative) charges, the zeta potential of the spores may be adjusted to positive (cationic) values through modification by PECs formulated at R values >1.0 at pH values of about 7.0. Such an embodiment may for example be advantageous in adhering beneficial nitrogen fixing bacteria to seeds or roots of crops. In such an application, the PECs should be nontoxic to the bacteria generated by germination of the spores under favorable conditions. In this example, PECs produced via dilution of PEC precursor solutions PDS2 and PDS2A described in Example 10 (R value of 4.0) were used to modify the surfaces of *Bacillus subtilis* spores, providing spores with positive (cationic) zeta potentials, as discussed above.

Serial dilution of concentrated cell suspensions followed by plating on a solid growth medium is a common way to determine the viable cells, or colony forming units (CFU), in the suspension. The CFU multiplied by the relevant dilution factor relates back to the viable microbes in the original suspension. Those skilled in the art recognize that the automated spreading of microbial suspension in a spiral formation from the center to the periphery of a circular plate containing solid microbial growth medium simultaneously accomplishes dilution and CFU determination of a microbial spore suspension through deposition over an ever lengthening area of the solid medium. Standard recognition software can visualize colonies on the solid medium and calculate the CFU/ml of the original suspension based on the distance and number of colonies relative to the center of the plate. Such an approach is implemented with commercially available equipment, such as the Autoplater Model AP5000 (Advanced Instruments). The inventors have utilized this method to determine the viability of *Bacillus subtilus* spores modified by the PECs of the instant invention.

Spores were suspended at $1\times10^6$ CFU/ml in formulation PDS2, PDS2A or sterile water. The spore suspension was then further diluted 1:100 in sterile distilled deionized water and spiral plated. After overnight incubation at 37° C. to allow growth and visualization of colonies, the CFU values were determined. The results in Table 12.1 below show that the PEC solutions did not interfere with the ability of the spores to form colonies when placed on growth medium, i.e. no significant differences between the number of viable spores in the control or modified spore dispersions are detected. Thus, although the cationic polymer poly(DADMAC) is present in the PECs formed from dilution of the PEC precursor solutions, there is no toxicity to the spores observed which might be due to this polymer. Of course, where germicidal characteristics are desired, a quaternary ammonium compound or other germicidal surfactant may be included.

TABLE 12.1

Viability of Modified *Bacillus subtilus* Spores Determined Via Spiral Plating

| Formulation | CFU/ml Observed |
|---|---|
| Control - Spore suspension only | $1.14 \times 10^4$ |
| Spore Suspension Exposed to PDS2 | $1.13 \times 10^4$ |
| Spore Suspension Exposed to PDS2A | $9.04 \times 10^3$ |

Example 13

Modification of Solid Surfaces by PEC Compositions Prepared Via Dilution of Precursor Solutions and their Measurement by QCM-D

TABLE 13.1

PEC Compositions with Surfactants Produced Via Dilution of Precursors for Characterization by QCM-d

| Formulation Name | Precursor sample | Precursor, grams | Water, grams | Total polymer concentration, mM | R value | Succinic Acid, mM | Surfactant 1, grams | Surfactant 1, wt % | Surfactant 2, grams | Surfactant 2, wt % | Surfactant 3, grams | Surfactant 3, wt % | Comments |
|---|---|---|---|---|---|---|---|---|---|---|---|---|---|
| DADPAA 43 | DADPAA 10 | 1.95 | 497.05 | 1.5 | 4.0 | 1.0 | — | — | — | — | — | — | |
| DPQ 3 | DADPAA 10 | 1.95 | 497.05 | 1.5 | 4.0 | 1.0 | 5.0 | 0.40 | — | — | — | — | Quat into PECs |
| DPEA 1 | DADPAA 10 | 1.95 | 495.05 | 1.5 | 4.0 | 1.0 | — | — | 2.0 | 0.40 | — | — | SA7 into PECs |
| DPAO 4 | DADPAA 10 | 1.95 | 490.60 | 1.5 | 4.0 | 1.0 | — | — | — | — | 6.5 | 0.40 | LO into PECs |

Notes:
Surfactant 1: Quaternary ammonium surfactant; BTC 1010, Stepan Corp.; 40 wt % aqueous solution.
Surfactant 2: Ethoxylated alcohol surfactant; Ecosurf SA-7, Dow Chemical Corp.; 100% actives.
Surfactant 3: Amine oxide surfactant; Ammonyx LO, Stepan Corp.; 31 wt % aqueous solution.

TABLE 13.2

Characterization of PEC Compositions in Table 10.1 by QCM-D

| Formulation Name | R value | Surfactant wt % | Surfactant type | Mass Adsorbed, ng/cm$^2$ | Mass after Rinsing, ng/cm$^2$ |
|---|---|---|---|---|---|
| DADPAA 43 | 4.0 | 0.00 | None | 175 ± 6 | 188 ± 6 |
| DPQ 3 | 4.0 | 0.40 | Quaternary ammonium | 276 ± 30 | 140 ± 50 |
| DPEA 1 | 4.0 | 0.40 | Ethoxylated alcohol | 210 ± 25 | 175 ± 20 |
| DPAO 4 | 4.0 | 0.40 | Amine oxide | 196 ± 52 | 175 ± 55 |

Example 14

Crystal Growth Inhibition by PECs

A. Inhibition of Calcium Carbonate Crystal Growth by PECs in Laundry

Ashing or white residue on clothes during laundering may be caused by encrustation of the fibers by calcium carbonate precipitation. Calcium carbonate is a ubiquitous insoluble salt found in municipal hard water and is also a by-product of the laundering process. Ashing on fibers can be reduced by inhibition of calcium carbonate crystal growth. Polyelectrolyte complexes can inhibit crystal growth by incorporation of the PEC moiety into the crystal lattice so as to prevent further deposition of $Ca^{2+}$ ions onto the seeded crystal. The inhibition efficiency is a function of the R value of the PECs.

The ability of the polyelectrolyte complex to inhibit crystal growth can be measured by monitoring the change in turbidity of the solution upon the addition of the PEC solution. The following experimental procedure was followed:

300 ppm of 2:1 Calcium:Magnesium Chloride and 4.0 mM of Sodium bicarbonate were added to 1000 mL of deionized water to form calcium carbonate in-situ. 8.25% sodium hypochlorite solution with 130 mM total polymer as PEC precursor was added to this solution under constant stirring. This amounted to 0.22 mM total polymer in the diluted state. Turbidity of the solution was monitored with a Hach 2100-AN Turbidimeter instrument over a period of 60 minutes. 3 Different R values were studied: R=0.5 (anionic rich), R=1.33 (cationic rich) and R=4.0 (very cationic rich). Turbidity of hard water without PECs, and turbidity of sodium hypochlorite solution in hard water, also without PECs, was also measured for reference. The results are shown in Table 14.1 below, as well as FIG. 1.

TABLE 14.1

Control Compositions and PEC Compositions for Inhibiting Turbidity

| Raw Material | R = 0.5 wt % active | R = 1.3 wt % active | R = 4 wt % active |
|---|---|---|---|
| PolyDADMAC | 0.697 | 1.195 | 1.674 |
| PolyAcrylic Acid | 0.616 | 0.396 | 0.185 |
| Sodium Hypochlorite | 8.25 | 8.25 | 8.25 |
| Sodium Hydroxide | 0.347 | 0.104 | 0.104 |
| D.I. Water | Balance | balance | balance |

B. Inhibition of Crystal Growth of By-Products from Metal Oxidation Caused by Hypochlorite It has been demonstrated previously that the reaction of iron and manganese ions with hypochlorite can cause significant yellowing and fabric damage to fabrics during the wash process. The rust-like byproducts of this chemical reaction precipitate and readily attach to certain fabrics, causing a dingying effect on the fabrics. The fabrics will appear yellowed, dulled and dingy as a result. Without being bound by theory, it is generally believed that hypochlorite readily and rapidly oxidizes metal ions to their rust-like byproducts, i.e. iron oxidizing to rust or iron oxide. The use of polymeric sequestering agents acts as a dispersant, preventing the metal ions from depositing onto the fabric. Also, they may act as crystal growth inhibitors, helping to slow the aggregation of these rust-like byproducts.

The use of sequestering agents in preventing oxidized metal deposition. Similarly, the inventors observe that the PEC formulations described in the present application produce a similar effect when in the presence of Mn(II) and Fe(II) ions. A sample experimental procedure is as follows:

An aqueous solution of 1760 ppm Fe(II) and 275 ppm Mn(II) ions was mixed. The solution was separated into 250 ml aliquots. To each aliquot, 2 ml of the described PEC formula and/or virgin sodium hypochlorite (diluted to 8.25% activity) was added respectively. The solutions were mixed immediately, causing the formation of dark brown oxidized metal precipitate. A small unbrightened cotton swatch was added to each aliquot and stirred for 1 minute, allowing the solution to saturate the cotton. The swatches were removed from the solution and squeezed dry. The difference in whiteness was easily observed, as the PEC-treated fabric remained white, while the non-PEC treated fabric adsorbed a large amount of the rust-like precipitate and appeared very brown and dulled.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A dilutable composition comprising:
   1) an oxidant selected from the group consisting of hypohalous acid, hypohalite and combinations thereof;
   2) a polyelectrolyte complex precursor composition comprising:
      (a) a water-soluble first polyelectrolyte bearing a net cationic charge or capable of developing a net cationic charge wherein said first polyelectrolyte is a homopolymer;
      (b) about 0.001% to 0.19% by weight of a water-soluble second polyelectrolyte bearing a net anionic charge or capable of developing a net anionic charge wherein said second polyelectrolyte is selected from the group consisting of a homopolymer, a random copolymer, and mixtures thereof; and
      (c) wherein the dilutable composition is free of precipitates, synthetic block copolymers, silicone copolymers, cross-linked poly(acrylic) and cross-linked water-soluble polyelectrolyte;
      (d) wherein the composition has a viscosity of less than about 1,000 centipoise;
      (e) wherein the water-soluble first polyelectrolyte bearing a net cationic charge or capable of developing a net cationic charge comprises poly(diallyldimethyl ammonium chloride) and the water-soluble second polyelectrolyte bearing a net anionic charge or capable of developing a net anionic charge comprises poly(vinyl) sulfate, and wherein an R value denoting a molar ratio of cationic or potentially cationic groups to that of anionic or potentially anionic groups of the first and second respective polyelectrolytes of the composition is greater than 1; and
   3) wherein upon dilution, the composition forms a polyelectrolyte complex.

2. A concentrate composition comprising:
   (a) about 0.001% to about 5.0% by weight of a water-soluble first polyelectrolyte bearing a net cationic charge or capable of developing a net cationic charge wherein said first polyelectrolyte is a poly(diallyldimethyl ammonium chloride) homopolymer;
   (b) about 0.001% to 0.19% by weight of a water-soluble second polyelectrolyte bearing a net anionic charge or capable of developing a net anionic charge wherein said second polyelectrolyte is selected from the group consisting of poly(acrylic acid), a copolymer of acrylic acid and maleic acid, a copolymer of acrylic acid and styrene, a copolymer of styrene sulfonic acid and maleic acid, and mixtures thereof;
   (c) a hypochlorite;
   (d) wherein the composition is free of precipitates, synthetic block copolymers, silicone copolymers, cross-linked poly(acrylic) and cross-linked water-soluble polyelectrolyte;
   (e) wherein the composition has a viscosity of less than about 1,000 centipoise; and
   (f) wherein upon dilution, the concentrate composition forms a polyelectrolyte complex.

3. The composition of claim 2, wherein an R value denoting a molar ratio of cationic or potentially cationic groups to that of anionic or potentially anionic groups of the first and second respective polyelectrolytes of the composition is greater than 1.

* * * * *